(12) United States Patent
Selsted et al.

(10) Patent No.: US 12,186,368 B2
(45) Date of Patent: *Jan. 7, 2025

(54) COMPOSITIONS AND METHODS FOR TREATMENT OF PROTEASE MEDIATED DISEASE

(71) Applicant: The Regents of the University of California, Oakland, CA (US)

(72) Inventors: Michael E. Selsted, Pasadena, CA (US); Dat Q. Tran, Alhambra, CA (US)

(73) Assignee: The Regents of the University of California, Oakland, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/825,221

(22) Filed: Mar. 20, 2020

(65) Prior Publication Data

US 2020/0333024 A1    Oct. 22, 2020

Related U.S. Application Data

(63) Continuation of application No. 15/135,060, filed on Apr. 21, 2016, now Pat. No. 10,603,356, which is a continuation of application No. 14/491,661, filed on Sep. 19, 2014, now Pat. No. 9,346,866, which is a continuation of application No. 13/486,548, filed on Jun. 1, 2012, now Pat. No. 10,512,669.

(60) Provisional application No. 61/492,753, filed on Jun. 2, 2011.

(51) Int. Cl.

| | | |
|---|---|---|
| *A61K 38/17* | (2006.01) | |
| *A61K 9/00* | (2006.01) | |
| *A61K 38/10* | (2006.01) | |
| *A61K 38/12* | (2006.01) | |
| *A61K 38/55* | (2006.01) | |
| *C07K 14/47* | (2006.01) | |
| *F01P 5/04* | (2006.01) | |
| *F24F 5/00* | (2006.01) | |
| *F24F 6/16* | (2006.01) | |
| *B63J 3/00* | (2006.01) | |

(52) U.S. Cl.
CPC ........ *A61K 38/1729* (2013.01); *A61K 9/0053* (2013.01); *A61K 38/10* (2013.01); *A61K 38/12* (2013.01); *A61K 38/55* (2013.01); *C07K 14/4723* (2013.01); *F01P 5/04* (2013.01); *F24F 5/0007* (2013.01); *F24F 6/16* (2013.01); *B63J 2003/002* (2013.01); *F01P 2005/046* (2013.01); *F24F 2203/1028* (2013.01); *F24F 2203/1076* (2013.01)

(58) Field of Classification Search
None
See application file for complete search history.

(56) References Cited

U.S. PATENT DOCUMENTS

| | | |
|---|---|---|
| 5,753,618 A | 5/1998 | Cavanak et al. |
| 6,335,318 B1 | 1/2002 | Selsted et al. |
| 6,444,645 B1 | 9/2002 | Selsted et al. |
| 6,514,727 B1 | 2/2003 | Selsted et al. |
| 6,524,858 B1 | 2/2003 | Zelmanovic et al. |
| 6,696,559 B1 | 2/2004 | Selsted |
| 6,800,745 B1 | 10/2004 | Selsted |
| 6,890,537 B2 | 5/2005 | Selsted et al. |
| 7,119,070 B2 | 10/2006 | Selsted et al. |
| 7,452,598 B2 | 11/2008 | Shiao et al. |
| 7,462,598 B2 | 12/2008 | Selsted et al. |
| 9,346,866 B2 | 5/2016 | Selsted et al. |
| 9,517,612 B2 | 12/2016 | Huang |
| 10,512,669 B2 | 12/2019 | Selsted et al. |
| 10,603,356 B2 | 3/2020 | Selsted et al. |
| 2003/0162718 A1 | 8/2003 | Selsted et al. |
| 2004/0014669 A1 | 1/2004 | Selsted et al. |
| 2005/0261193 A1 | 11/2005 | Selsted et al. |
| 2006/0036083 A1 | 2/2006 | Moss et al. |
| 2006/0115480 A1 | 6/2006 | Hillman |
| 2008/0255052 A1 | 10/2008 | Selsted et al. |
| 2009/0042775 A1 | 2/2009 | Fagan et al. |
| 2009/0255052 A1 | 10/2009 | Booth |
| 2010/0210537 A1* | 8/2010 | Bevec ............... A61P 31/22 514/1.1 |
| 2011/0065771 A1 | 3/2011 | Colgan |
| 2013/0034597 A1 | 2/2013 | Maggio |

FOREIGN PATENT DOCUMENTS

| | | |
|---|---|---|
| CA | 2489244 A1 | 12/2003 |
| JP | 2017076042 | 4/2017 |
| JP | 2018166698 | 10/2019 |
| WO | WO-03105883 A1 | 12/2003 |

(Continued)

OTHER PUBLICATIONS

G. Dubin, Proteinaceous cysteine protease inhibitors, CMLS, Cell. Mol. Life Sci. 62 (2005) 653-669 (Year: 2005).*
Aktas B., et al., "Aspirin Induces Platelet Receptor Shedding via ADAM17 (TACE)," Journal of Biological Chemistry, Dec. 2, 2005, vol. 280 (48), pp. 39716-39722.
Alvarez-Iglesias, M., et al., "Continuous Real-time Measurement of Tumor Necrosis Factor-alpha Converting Enzyme Activity on Live Cells," Laboratory Investigation, 2005, vol. 85, pp. 1440-1448.
Berkestedt I., et al., "Elevated Plasma Levels of Antimicrobial Polypeptides in Patients with Severe Sepsis," Journal of Innate Immunity, 2010, vol. 2, pp. 478-482.
Blaydon D.C., et al., "Inflammatory Skin and Bowel Disease Linked to ADAM17 Deletion," The New England Journal of Medicine, Oct. 20, 2011, vol. 365 (16), pp. 1502-1508.

(Continued)

*Primary Examiner* — Thomas S Heard
(74) *Attorney, Agent, or Firm* — Fish IP Law, LLP

(57) ABSTRACT

A method is provided for a condition related to the activity of a protease through the administration of a θ-defensin, analog, or derivative is described. Suitable proteases include metalloproteases and cysteine proteases such as Cathepsin-C. The θ-defensin, analog, or derivative can be effectively administered parenterally, topically, or orally.

15 Claims, 9 Drawing Sheets

Specification includes a Sequence Listing.

(56) References Cited

FOREIGN PATENT DOCUMENTS

WO    WO-2007044998 A1 *  4/2007  ............ A61K 38/12

OTHER PUBLICATIONS

Blobel C. P., "ADAMs: Key Components in EGFR Signalling and Development," Nature Reviews Molecular Cell Biology, 2005, vol. 6, pp. 32-43.
Brand D.D., et al., "The Mouse Model of Collagen-induced Arthritis," Methods in Molecular Medicine, 2004, vol. 102, pp. 295-312.
Cheng L., et al., "Discovery of Antibacterial Cyclic Peptides that Inhibit the ClpXP Protease," Protein Science, 2007, vol. 16 (8), pp. 1535-1542.
Cole A.M., et al., "Minidefensins: Antimicrobial Peptides with Activity against HIV-1," Current Pharmaceutical Design, 2003, vol. 9, pp. 1463-1473.
Cole A.M., et al., "Retrocyclin: A Primate Peptide that Protects Cells from Infection by T- and M-tropic strains of HIV-1," Proceedings of the National Academy of Sciences of the United States of America, 2002, vol. 99, pp. 1813-1818.
Colon A.L., et al., "Implications of TNF-α Convertase (TACE/ADAM17) in Inducible Nitric Oxide Synthase Expression and Inflammation in Experimental Model of Colitis," Cytokine, Dec. 2001, vol. 16 (6021), pp. 220-226.
Conibear, A.C., et al., "The Chemistry and Biology of Theta Defensins," Angewandte Reviews, 2014, vol. 53, pp. 10612-10623, Wiley-VCH Verlag GmbH & Co. Weinheim.
Feldmann M., et al., "Lasker Clinical Medical Research Award, TNF Defined as a Therapeutic Target for rheumatoid Arthritis and Other Autoimmune Diseases," Nature Medicine, 2003, vol. 9, pp. 1245-1250.
Firestein G.S., "Evolving Concepts of Rheumatoid Arthritis," Nature, 2003, vol. 423, pp. 356-361.
Garcia A.E., et al., "Isolation, Synthesis, and Antimicrobial Activities of Naturally Occurring theta-defensin Isoforms from Baboon Leukocytes," Infection and Immunity, 2008, vol. 76 (12), pp. 5883-5891.
Giacometti A., et al., "Cathelicidin Peptide Sheep Myeloid Antimicrobial Peptide-29 Prevents Endotoxin-induced Mortality in Rat Models of Septic Shock," American Journal of Respiratory and Critical Care Medicine, 2004, vol. 169, pp. 187-194.
Giacometti A., et al., "Potential Therapeutic Role of Cationic Peptides in Three Experimental Models of Septic Shock," Antimicrobial Agents and Chemotherapy, 2002, vol. 46, pp. 2132-2136.
Highlight Health, New Drug Failure Rates Rising in Phase II and III Clinical Trials, Medcitizens, 2011, pp. 1-8. Retrieved from the Internet [https://medcitynews.com/2011/06/new-drug-failure-rates-rising-in-phase-ii-and-iii-clinical-trials/].
Hubbard W.J., et al., "Cecal Ligation and Puncture," Shock, 2005, vol. 24 (Suppl 1), pp. 52-57.
International Search Report and Written Opinion for Application No. PCT/US2012/040455, mailed on Sep. 14, 2012, 14 pages.
Jarczak J., et al., "Defensins: Natural Component of Human Innate Immunity," Human Immunology, Institute of Genetics and Animal Breeding, Polish Academy of Sciences in Jastrzebiec, Poland, Jun. 10, 2013, vol. 74, pp. 1069-1079.
McInnes I.B., et al., "State-of-the-art: Rheumatoid Arthritis," Annals of the Rheumatic Diseases, 2010, vol. 69, pp. 1898-1906.
Molina M.A., et al., "Trastuzumab (Herceptin), A Humanized Anti-HER2 Receptor Monoclonal Antibody, Inhibits Basal and Activated HER2 Ectodomain Cleavage in Breast Cancer Cells," Cancer Research, 2001, vol. 61, pp. 4744-4749.

Moss M.L., et al., "ADAM10 as a Target for Anti-cancer Therapy," Current Pharmaceutical Biotechnology, 2008, vol. 9, pp. 2-8.
Moss M.L., et al., "Drug insight: Tumor Necrosis Factor-converting Enzyme as a Pharmaceutical Target for Rheumatoid Arthritis," Nature Clinical Practice Rheumatology, 2008, vol. 4 (6), pp. 300-309.
Motzkus D., et al., "The Novel beta-defensin DEFB123 prevents Lipopolysaccharide-mediated Effects in Vitro and in Vivo," The FASEB Journal, 2006, vol. 20, pp. 1701-1702.
Murphy G., et al., "Reappraising Metalloproteinases in Rheumatoid Arthritis and Osteoarthritis: Destruction or Repair?," Nature Clinical Practice Rheumatology, 2008, vol. 4 (3), pp. 128-135.
Murumkar P.R., et al., "Novel TACE Inhibitors in Drug Discovery: A Review of Patented Compounds," Expert Opinion on Therapeutic Patents, 2010, vol. 20 (1), pp. 31-57.
NCBI., "Macaca Mulatta Theta Defensin 1a Precursor, mRNA, Complete CDS," Nucleotide, NCBI, Jun. 30, 2019, 1 page.
Panyutich A.V., et al., "Plasma Defensin Concentrations are Elevated in Patients with Septicemia or Bacterial Meningitis," Journal of Laboratory and Clinical Medicine, 1993, vol. 122, pp. 202-207.
Polymedix, Inc., "PMX-30063 The First and Only Defensin Mimetic Systemic Antibiotic Drug in Human Clinical Trials," Medical News Today, Oct. 2008, Retrieved from the internet [http://www.medicalnewstoday.com/releases/118978.php], 4 Pages.
Rosenfeld Y., et al., "Lipopolysaccharide (Endotoxin)-host Defense Antibacterial Peptides Interactions: Role in Bacterial Resistance and Prevention of Sepsis," Biochimica et Biophysica Acta, 2006, vol. 1758, pp. 1513-1522.
Rosloniec E.F., et al., "Collagen-induced Arthritis," Current Protocol Immunology, Apr. 2010, Chapter 15, vol. 89, Unit 15, pp. 15.5.1-15.5.25.
Schaal J.B., et al., "Macrocyclic θ-defensins Suppress Tumor Necrosis Factor-α(TNF-α) Shedding by Inhibition of TNF-α-converting Enzyme," Journal of Biological Chemistry, 2018, vol. 293 (8), pp. 2725-2734.
Selsted M.E., et al., "Mammalian Defensins in the Antimicrobial Immune Response," Nature Immunology, Jun. 2005, vol. 6 (6), pp. 551-557.
Selsted M.E., et al., "Theta-defensins: Cyclic Antimicrobial Peptides Produced by Binary Ligation of Truncated Alpha-defensins," Current Protein and Peptide Science, 2004, vol. 5, pp. 365-371.
Tang Y.Q., et al., "A Cyclic Antimicrobial Peptide Produced in Primate Leukocytes by the Ligation of Two Truncated alpha-defensins," Science, 1999, vol. 286, pp. 498-502.
Tongaonkar P., et al., "Rhesus Macaque 0-defensin Isoforms: Expression, Antimicrobial Activities, and Demonstration of a Prominent Role in Neutrophil Granule Microbicidal Activities," Journal of Leukocyte Biology, 2011, vol. 89, pp. 283-290.
Tran D., et al., "Homodimeric θ-defensins from Rhesus Macaque Leukocytes: Isolation, Synthesis, Antimicrobial Activities, and Bacterial Binding Properties of the Cyclic Peptides," Journal of Biological Chemistry, 2002, vol. 277 (5), pp. 3079-3084.
Tran D., et al., "Microbicidal Properties and Cytocidal Selectivity of Rhesus Macaque θ-defensins," Antimicrobial Agents and Chemotherapy, 2008, vol. 52 (3), pp. 944-953.
Vingsbo C., et al., "Pristane-induced Arthritis in Rats: A New Model for Rheumatoid Arthritis with a Chronic Disease Course Influenced by Both Major Histocompatibility Complex and Non-major Histocompatibility Complex Genes," The American Journal of Pathology, 1996, vol. 149 (5), pp. 1675-1683.
Wang W., et al., "Activity of alpha- and theta-defensins Against Primary Isolates of HIV-1," Journal of Immunology, 2004, vol. 173, pp. 515-520.
Wang W., "Retrocyclin, An Antiretroviral Theta-defensin, Is a Lectin," Journal of Immunology, 2003, vol. 170, pp. 4708-4716.

(56) References Cited

OTHER PUBLICATIONS

Wermuth C.G., (Chairman), et al., "Glossary of Terms Used in Medicinal Chemistry (IUPAC Recommendations 1998)," Pure and Applied Chemistry, 1998, vol. 70 (5), pp. 1129-1143.
Wohlford-Lenane C.L., et al., "Rhesus theta-defensin prevents Death in a Mouse Model of Severe Acute Respiratory Syndrome Coronavirus Pulmonary Disease," Journal of Virology, 2009, vol. 83, pp. 11385-11390.

* cited by examiner

SEQUENCE LISTING

```
<160> NUMBER OF SEQ ID NOS: 38

<210> SEQ ID NO 1
<211> LENGTH: 500
<212> TYPE: DNA
<213> ORGANISM: Macaca mulatta
<220> FEATURE:
<221> NAME/KEY: misc_feature
<222> LOCATION: (1)..(500)
<223> OTHER INFORMATION: theta defensin 1a precursor (RTD1A), mRNA

<400> SEQUENCE: 1
gacggctgct gttgctacag gagacccagg acagaggact gctgtctgca ctctctcttc      60
actctgccta acttgaggat ctgtcactcc agccatgagg accttcgccc tcctcaccgc     120
catgcttctc ctggtggccc tgcacgctca ggcagaggca cgtcaggcaa gagctgatga     180
agctgccgcc cagcagcagc ctggaacaga tgatcaggga atggctcatt cctttacatg     240
gcctgaaaac gccgctcttc cactttcaga gtcagcgaaa ggcttgaggt gcatttgcac     300
acgaggattc tgccgtttgt tataatgtca ccttgggtcc tgcgcttttc gtggttgact     360
ccaccggatc tgctgccgct gagcttccag aatcaagaaa aatatgctca gaagttactt     420
tgagagttaa aagaaattct tgctactgct gtaccttctc ctcagtttcc ttttctcatc     480
ccaaataaat accttatcgc                                                 500

<210> SEQ ID NO 2
<211> LENGTH: 460
<212> TYPE: DNA
<213> ORGANISM: Macaca mulatta
<220> FEATURE:
<221> NAME/KEY: misc_feature
<222> LOCATION: (1)..(460)

<400> SEQUENCE: 2
gtctgccctc tctgctcgcc ctgcctaact tgaggatctg tcactccagc catgaggacc      60
tttgccctcc tcactgccat gcttctcctg gtggccctgc acgctcaggc agaggcacgt     120
caggcaagag ctgatgaagc tgccgcccag cagcagcctg gagcagacga tcagggaatg     180
gctcattcct ttacacggcc tgaaaacgcc gctcttccgc tttcagagtc agcgagaggc     240
ttgaggtgcc tttgcagacg aggagtttgc caactgttat aaaggcgttt ggggtcctgc     300
gcttttcgtg gttgactctg ccggatctgc tgccgctgag cttccagaat caagaaaat     360 acgctcagaa gttactttga gagttgaaag aaattcctgt tactcctgta ccttgtcctc     420
aatttccttt tctcatccca aataaatacc ttctcgcaag                           460
```

<210> SEQ ID NO 3
<211> LENGTH: 421
<212> TYPE: DNA
<213> ORGANISM: Macaca mulatta
<220> FEATURE:
<221> NAME/KEY: misc_feature
<222> LOCATION: (1)..(421)
<223> OTHER INFORMATION: demidefensin 3 (LOC574121), mRNA

<400> SEQUENCE: 3

| | | | | | |
|---|---|---|---|---|---|
| gtgaccccag | ccatgaggac | cctcgccctc | cacactgcca | tgcttctcct | ggtggccctg | 60 |
| cacgctcagg | cagaggcacg | tcaggcaaga | gctgatgaag | ctgccgccca | gcagcagcct | 120 |
| ggagcagatg | atcagggaat | ggctcactcc | tttacatggc | ctgaaaacgc | cgctcttccg | 180 |
| ctttcagagt | cagagagagg | cttgaggtgc | atttgcgtac | taggaatttg | ccgtctgtta | 240 |
| taacggcatt | tgcggtcctg | cgacttttgt | ggttgactct | atcggatctg | ttgccgctga | 300 |
| gcttgcagaa | tcaagaaaaa | caagctcaga | agttactttg | agagttaaaa | gaaattcttg | 360 |
| ttactcctct | accttgccct | aaatttcctt | ttctcatccc | aaataaatac | cttctcgcaa | 420 |
| g | | | | | | 421 |

<210> SEQ ID NO 4
<211> LENGTH: 514
<212> TYPE: DNA
<213> ORGANISM: Papio anubis
<220> FEATURE:
<221> NAME/KEY: misc_feature
<222> LOCATION: (1)..(514)
<223> OTHER INFORMATION: theta defensin a precursor (BTD-a) mRNA, complete cds

<400> SEQUENCE: 4

| | | | | | |
|---|---|---|---|---|---|
| agacctggga | cagaggactg | ctgtctgcac | tctctcttca | ctctgcctaa | cttgacgatc | 60 |
| tgtcactcca | gccatgagga | ccttcgccct | cctcaccgcc | atgcttctcc | tggtggccct | 120 |
| gcatgctcag | gcagaggcac | gtcaggcaag | agctgatgaa | gctgctgccc | agcagcagcc | 180 |
| tggagcagat | gatcagggaa | tggctcattc | ctttacatgg | cctgaaaacg | ccgctcttcc | 240 |
| gctttcagag | tcagcgaaag | gcttgaggtg | cgtttgcaca | cgaggattct | gccgtttgtt | 300 |
| ataatgtcac | cttgggtcct | gcgccttttca | tggttgactc | caccggatct | gctgccgctg | 360 |
| agcttccaga | atcaagaaaa | atacgctcag | aagttacttt | gagagttaca | agaaattctt | 420 |
| gctactgctg | taccttctcc | tcagtttcct | tttctcatcc | caaataaata | ccttatcgca | 480 |
| agaaaaaaaa | aaaaaaaaaa | aaaaaaaaaa | aaaa | | | 514 |

<210> SEQ ID NO 5
<211> LENGTH: 504
<212> TYPE: DNA
<213> ORGANISM: Papio anubis
<220> FEATURE:
<221> NAME/KEY: misc_feature
<222> LOCATION: (1)..(504)
<223> OTHER INFORMATION: theta defensin b (BTDB), mRNA

<400> SEQUENCE: 5

| | | | | | |
|---|---|---|---|---|---|
| agacccggga | cagaggactg | ctgtctgccc | tctctcttca | ctctgcctaa | cttgaggatc | 60 |
| tgtcactcca | gccatgagga | cctttgccct | cctcaccgcc | atgcttctcc | tggtggccct | 120 |
| gcagcctcag | gcagaggcac | gtcaggcaag | agctgatgaa | gctgccgccc | agcagcagcc | 180 |
| tggagcagat | gatcagggaa | tggctcattc | ctttacacgg | cctgaaaacg | ccgctcttcc | 240 |
| actttcagag | tcagcgaaag | gcttgaggtg | cgtttgcaga | cgaggagttt | gccaactgtt | 300 |

```
ataaaggcgt tgggggtcct gcgcttttcg tggttgactc tgtcagatct gctgccgctg    360
agcttccaga atcaagaaaa atacgctcag aagttacttt gagagttgaa agaaattctt    420
gttactcctg taccttgtcc tcaatttcct tttctcatcc caaataaata ccttctcgca    480
aaaaaaaaaa aaaaaaaaaa aaaa                                           504
```

<210> SEQ ID NO 6
<211> LENGTH: 542
<212> TYPE: DNA
<213> ORGANISM: Papio anubis
<220> FEATURE:
<221> NAME/KEY: misc_feature
<222> LOCATION: (1)..(542)
<223> OTHER INFORMATION: theta defensin c (BTDC), mRNA

<400> SEQUENCE: 6

```
agacccggga cagaggactg ctgtctgccc tctctggtca ctctgcgtag cacaaggatc    60
tgtcactcca gccatgagga ccttcgcctt cctcactgcc atgcttctcc tggtggccct    120
gcacgcacag gcagaggcac gtcaggcaag agctgatgaa gctgccatcc aggagcagcc    180
tggagcagat gatcagggaa tggctcattc ctttacacgg aatgaaagtg ccgttcttcc    240
gctttcagag tcagagagag gcttgaggtg catttgctta ctaggaattt gccgtctgtt    300
ataacggcgt ttgcggtcct gcgactttcg tggttgactc tatcggatct gttgccactg    360
agcttgcaga atcaagaaaa accagctcag aagttacttt gagagttaaa agaaattctt    420
gttactcctc taccttgccc tcaatttcct tttctcatcc caaataaata ccttgtcgca    480
agaaaaaaaa agaaaaaaaa aaaaaaaaaa aaaaaaaaaa aaaaaaaaaa aaaaaaaaaa    540
aa                                                                   542
```

<210> SEQ ID NO 7
<211> LENGTH: 258
<212> TYPE: DNA
<213> ORGANISM: Papio anubis
<220> FEATURE:
<221> NAME/KEY: misc_feature
<222> LOCATION: (1)..(258)
<223> OTHER INFORMATION: theta defensin d (LOC100196942), mRNA

<400> SEQUENCE: 7

```
actccagcca tgaggacctt tgccctcctc accgccatgc ttctcctggt ggccctgcag    60
gctcaggcag aggcacgtca ggcaagagct gatgaagctg ccgcccagca gcagcctgga    120
gcagatgatc agggaatggc tcattccttt acacggcctg aaaacgccgc tcttcctctt    180
tcagagtcag cgaaaggctt gaggtgcttt tgcagacgag gagtttgcca actgttataa    240
aggcgcttgg ggtcctgc                                                  258
```

<210> SEQ ID NO 8
<211> LENGTH: 18
<212> TYPE: PRT
<213> ORGANISM: Macaca mulatta
<220> FEATURE:
<221> NAME/KEY: PEPTIDE
<222> LOCATION: (1)..(18)
<223> OTHER INFORMATION: RTD-1, cyclic peptide

<400> SEQUENCE: 8

Gly Phe Cys Arg Cys Leu Cys Arg Arg Gly Val Cys Arg Cys Ile Cys
1               5                   10                  15

Thr Arg

```
<210> SEQ ID NO 9
<211> LENGTH: 76
<212> TYPE: PRT
<213> ORGANISM: Macaca mulatta
<220> FEATURE:
<221> NAME/KEY: PEPTIDE
<222> LOCATION: (1)..(76)
<223> OTHER INFORMATION: RTD1b

<400> SEQUENCE: 9

Met Arg Thr Leu Ala Leu His Thr Ala Met Leu Leu Val Ala Leu
1               5                   10                  15

His Ala Gln Ala Glu Ala Arg Gln Ala Arg Ala Asp Glu Ala Ala Ala
            20                  25                  30

Gln Gln Gln Pro Gly Ala Asp Asp Gln Gly Met Ala His Ser Phe Thr
        35                  40                  45

Trp Pro Glu Asn Ala Ala Leu Pro Leu Ser Glu Ser Ala Arg Gly Leu
    50                  55                  60

Arg Cys Ile Cys Val Leu Gly Ile Cys Arg Leu Leu
65                  70                  75

<210> SEQ ID NO 10
<211> LENGTH: 76
<212> TYPE: PRT
<213> ORGANISM: Macaca mulatta
<220> FEATURE:
<221> NAME/KEY: PEPTIDE
<222> LOCATION: (1)..(76)
<223> OTHER INFORMATION: RTD1c

<400> SEQUENCE: 10

Met Arg Thr Leu Ala Leu His Thr Ala Met Leu Leu Val Ala Leu
1               5                   10                  15

His Ala Gln Ala Glu Ala Arg Gln Ala Arg Ala Asp Glu Ala Ala Ala
            20                  25                  30

Gln Gln Gln Pro Gly Ala Asp Asp Gln Gly Met Ala His Ser Phe Thr
        35                  40                  45

Trp Pro Glu Asn Ala Ala Leu Pro Leu Ser Glu Ser Ala Arg Gly Leu
    50                  55                  60

Arg Cys Ile Cys Val Leu Gly Ile Cys Arg Leu Leu
65                  70                  75

<210> SEQ ID NO 11
<211> LENGTH: 14
<212> TYPE: PRT
<213> ORGANISM: Artificial Sequence
<220> FEATURE:
<223> OTHER INFORMATION: Synthettic cyclic tetradecapeptide RTD-1-27
<220> FEATURE:
<221> NAME/KEY: PEPTIDE
<222> LOCATION: (1)..(14)
<223> OTHER INFORMATION: RTD-1-27

<400> SEQUENCE: 11

Gly Phe Cys Arg Cys Arg Arg Gly Val Cys Arg Cys Thr Arg
1               5                   10

<210> SEQ ID NO 12
<211> LENGTH: 14
<212> TYPE: PRT
<213> ORGANISM: Artificial Sequence
<220> FEATURE:
<223> OTHER INFORMATION: Synthetic cyclic tetradecapeptide RTD-1-28
```

```
<220> FEATURE:
<221> NAME/KEY: RTD-1-28
<222> LOCATION: (1)..(14)
<223> OTHER INFORMATION: synthetic peptide
<220> FEATURE:
<221> NAME/KEY: PEPTIDE
<222> LOCATION: (1)..(14)
<223> OTHER INFORMATION: RTD-1-28

<400> SEQUENCE: 12

Gly Val Cys Ile Val Arg Arg Arg Phe Cys Leu Cys Arg Arg
1               5                   10

<210> SEQ ID NO 13
<211> LENGTH: 14
<212> TYPE: PRT
<213> ORGANISM: Artificial Sequence
<220> FEATURE:
<223> OTHER INFORMATION: Synthetic cyclic tetradecapeptide RTD-1-29
<220> FEATURE:
<221> NAME/KEY: PEPTIDE
<222> LOCATION: (1)..(14)
<223> OTHER INFORMATION: RTD-1-29

<400> SEQUENCE: 13

Gly Val Cys Leu Cys Ile Arg Gly Arg Cys Arg Cys Arg Arg
1               5                   10

<210> SEQ ID NO 14
<211> LENGTH: 18
<212> TYPE: PRT
<213> ORGANISM: Macaca mulatta
<220> FEATURE:
<221> NAME/KEY: PEPTIDE
<222> LOCATION: (1)..(18)
<223> OTHER INFORMATION: RTD-2, cyclic peptide

<400> SEQUENCE: 14

Gly Val Cys Arg Cys Leu Cys Arg Arg Gly Val Cys Arg Cys Leu Cys
1               5                   10                  15

Arg Arg

<210> SEQ ID NO 15
<211> LENGTH: 18
<212> TYPE: PRT
<213> ORGANISM: Macaca mulatta
<220> FEATURE:
<221> NAME/KEY: PEPTIDE
<222> LOCATION: (1)..(18)
<223> OTHER INFORMATION: RTD-3, cyclic peptide

<400> SEQUENCE: 15

Gly Phe Cys Arg Cys Ile Cys Thr Arg Gly Phe Cys Arg Cys Ile Cys
1               5                   10                  15

Thr Arg

<210> SEQ ID NO 16
<211> LENGTH: 18
<212> TYPE: PRT
<213> ORGANISM: Macaca mulatta
<220> FEATURE:
<221> NAME/KEY: PEPTIDE
<222> LOCATION: (1)..(18)
<223> OTHER INFORMATION: RTD-4, cyclic peptide

<400> SEQUENCE: 16

Gly Ile Cys Arg Cys Ile Cys Thr Arg Gly Phe Cys Arg Cys Ile Cys
1               5                   10                  15
```

Val Leu

<210> SEQ ID NO 17
<211> LENGTH: 18
<212> TYPE: PRT
<213> ORGANISM: Macaca mulatta
<220> FEATURE:
<221> NAME/KEY: PEPTIDE
<222> LOCATION: (1)..(18)
<223> OTHER INFORMATION: RTD-5, cyclic peptide

<400> SEQUENCE: 17

Gly Ile Cys Arg Cys Leu Cys Arg Arg Gly Val Cys Arg Cys Ile Cys
1               5                   10                  15

Val Leu

<210> SEQ ID NO 18
<211> LENGTH: 18
<212> TYPE: PRT
<213> ORGANISM: Macaca mulatta
<220> FEATURE:
<221> NAME/KEY: PEPTIDE
<222> LOCATION: (1)..(18)
<223> OTHER INFORMATION: RTD-6, cyclic peptide

<400> SEQUENCE: 18

Gly Ile Cys Arg Cys Ile Cys Val Leu Gly Ile Cys Arg Cys Ile Cys
1               5                   10                  15

Val Leu

<210> SEQ ID NO 19
<211> LENGTH: 18
<212> TYPE: PRT
<213> ORGANISM: Macaca mulatta
<220> FEATURE:
<221> NAME/KEY: PEPTIDE
<222> LOCATION: (1)..(18)
<223> OTHER INFORMATION: BTD-1, cyclic peptide

<400> SEQUENCE: 19

Cys Val Cys Arg Arg Gly Val Cys Arg Cys Val Cys Thr Arg Gly Phe
1               5                   10                  15

Cys Arg

<210> SEQ ID NO 20
<211> LENGTH: 18
<212> TYPE: PRT
<213> ORGANISM: Macaca mulatta
<220> FEATURE:
<221> NAME/KEY: PEPTIDE
<222> LOCATION: (1)..(18)
<223> OTHER INFORMATION: BTD-2, cyclic peptide

<400> SEQUENCE: 20

Cys Val Cys Arg Arg Gly Val Cys Arg Cys Val Cys Arg Arg Gly Val
1               5                   10                  15

Cys Arg

<210> SEQ ID NO 21
<211> LENGTH: 18
<212> TYPE: PRT
<213> ORGANISM: Macaca mulatta
<220> FEATURE:
<221> NAME/KEY: PEPTIDE
<222> LOCATION: (1)..(18)

<223> OTHER INFORMATION: BTD-3, cyclic peptide

<400> SEQUENCE: 21

Cys Ile Cys Leu Leu Gly Ile Cys Arg Cys Val Cys Thr Arg Gly Phe
1               5                   10                  15

Cys Arg

<210> SEQ ID NO 22
<211> LENGTH: 18
<212> TYPE: PRT
<213> ORGANISM: Macaca mulatta
<220> FEATURE:
<221> NAME/KEY: PEPTIDE
<222> LOCATION: (1)..(18)
<223> OTHER INFORMATION: BTD-4, cyclic peptide

<400> SEQUENCE: 22

Cys Ile Cys Leu Leu Gly Ile Cys Arg Cys Val Cys Arg Arg Gly Val
1               5                   10                  15

Cys Arg

<210> SEQ ID NO 23
<211> LENGTH: 18
<212> TYPE: PRT
<213> ORGANISM: Macaca mulatta
<220> FEATURE:
<221> NAME/KEY: PEPTIDE
<222> LOCATION: (1)..(18)
<223> OTHER INFORMATION: BTD-5, cyclic peptide

<400> SEQUENCE: 23

Cys Ile Cys Leu Leu Gly Ile Cys Arg Cys Val Cys Arg Arg Gly Val
1               5                   10                  15

Cys Arg

<210> SEQ ID NO 24
<211> LENGTH: 18
<212> TYPE: PRT
<213> ORGANISM: Macaca mulatta
<220> FEATURE:
<221> NAME/KEY: PEPTIDE
<222> LOCATION: (1)..(18)
<223> OTHER INFORMATION: BTD-6, cyclic peptide

<400> SEQUENCE: 24

Ile Cys Leu Leu Gly Ile Cys Arg Cys Ile Cys Leu Leu Gly Ile
1               5                   10                  15

Cys Arg

<210> SEQ ID NO 25
<211> LENGTH: 18
<212> TYPE: PRT
<213> ORGANISM: Macaca mulatta
<220> FEATURE:
<221> NAME/KEY: PEPTIDE
<222> LOCATION: (1)..(18)
<223> OTHER INFORMATION: BTD-7, cyclic peptide

<400> SEQUENCE: 25

Cys Phe Cys Arg Arg Gly Val Cys Arg Cys Val Cys Thr Arg Gly Phe
1               5                   10                  15

Cys Arg

<210> SEQ ID NO 26

```
<211> LENGTH: 18
<212> TYPE: PRT
<213> ORGANISM: Macaca mulatta
<220> FEATURE:
<221> NAME/KEY: PEPTIDE
<222> LOCATION: (1)..(18)
<223> OTHER INFORMATION: BTD-8, cyclic peptide

<400> SEQUENCE: 26

Cys Phe Cys Arg Arg Gly Val Cys Arg Cys Val Cys Arg Arg Gly Val
1               5                   10                  15

Cys Arg

<210> SEQ ID NO 27
<211> LENGTH: 18
<212> TYPE: PRT
<213> ORGANISM: Macaca mulatta
<220> FEATURE:
<221> NAME/KEY: PEPTIDE
<222> LOCATION: (1)..(18)
<223> OTHER INFORMATION: BTD-9, cyclic peptide

<400> SEQUENCE: 27

Cys Phe Cys Arg Arg Gly Val Cys Arg Cys Ile Cys Leu Leu Gly Ile
1               5                   10                  15

Cys Arg

<210> SEQ ID NO 28
<211> LENGTH: 18
<212> TYPE: PRT
<213> ORGANISM: Macaca mulatta
<220> FEATURE:
<221> NAME/KEY: PEPTIDE
<222> LOCATION: (1)..(18)
<223> OTHER INFORMATION: BTD-10, cyclic peptide

<400> SEQUENCE: 28

Cys Phe Cys Arg Arg Gly Val Cys Arg Cys Phe Cys Phe Phe Gly Val
1               5                   10                  15

Cys Arg

<210> SEQ ID NO 29
<211> LENGTH: 76
<212> TYPE: PRT
<213> ORGANISM: Homo sapiens
<220> FEATURE:
<221> NAME/KEY: PEPTIDE
<222> LOCATION: (1)..(76)
<223> OTHER INFORMATION: Human theta defensin pseudogene, HTDp

<400> SEQUENCE: 29

Met Arg Thr Phe Ala Leu Leu Thr Ala Met Leu Leu Leu Val Ala Leu
1               5                   10                  15

His Ala Gln Ala Glu Pro Leu Gln Ala Arg Ala Asp Glu Ala Ala Ala
                20                  25                  30

Gln Glu Gln Pro Gly Ala Asp Asp Gln Glu Met Ala His Ala Phe Thr
            35                  40                  45

Trp His Glu Ser Ala Ala Leu Pro Leu Ser Asp Ser Ala Arg Gly Leu
        50                  55                  60

Arg Cys Ile Cys Gly Arg Gly Ile Cys Arg Leu Leu
65                  70                  75

<210> SEQ ID NO 30
<211> LENGTH: 30
```

```
<212> TYPE: PRT
<213> ORGANISM: Homo sapiens
<220> FEATURE:
<221> NAME/KEY: PEPTIDE
<222> LOCATION: (1)..(30)
<223> OTHER INFORMATION: Human alpha defensin, HNP-1

<400> SEQUENCE: 30

Ala Cys Tyr Cys Arg Ile Pro Ala Cys Ile Ala Gly Glu Arg Arg Tyr
1               5                   10                  15

Gly Thr Cys Ile Tyr Gln Gly Arg Leu Trp Ala Phe Cys Cys
            20                  25                  30

<210> SEQ ID NO 31
<211> LENGTH: 29
<212> TYPE: PRT
<213> ORGANISM: Homo sapiens
<220> FEATURE:
<221> NAME/KEY: PEPTIDE
<222> LOCATION: (1)..(29)
<223> OTHER INFORMATION: Human alpha defensin HNP-2

<400> SEQUENCE: 31

Cys Tyr Cys Arg Ile Pro Ala Cys Ile Ala Gly Glu Arg Arg Tyr Gly
1               5                   10                  15

Thr Cys Ile Tyr Gln Gly Arg Leu Trp Ala Phe Cys Cys
            20                  25

<210> SEQ ID NO 32
<211> LENGTH: 30
<212> TYPE: PRT
<213> ORGANISM: Homo sapiens
<220> FEATURE:
<221> NAME/KEY: PEPTIDE
<222> LOCATION: (1)..(30)
<223> OTHER INFORMATION: Human alpha defensin HNP-3

<400> SEQUENCE: 32

Asp Cys Tyr Cys Arg Ile Pro Ala Cys Ile Ala Gly Glu Arg Arg Tyr
1               5                   10                  15

Gly Thr Cys Ile Tyr Gln Gly Arg Leu Trp Ala Phe Cys Cys
            20                  25                  30

<210> SEQ ID NO 33
<211> LENGTH: 33
<212> TYPE: PRT
<213> ORGANISM: Homo sapiens
<220> FEATURE:
<221> NAME/KEY: PEPTIDE
<222> LOCATION: (1)..(33)
<223> OTHER INFORMATION: Human alpha defensin HNP-4

<400> SEQUENCE: 33

Val Cys Ser Cys Arg Leu Val Phe Cys Arg Arg Thr Glu Leu Arg Val
1               5                   10                  15

Gly Asn Cys Leu Ile Gly Gly Val Ser Phe Thr Tyr Cys Cys Thr Arg
            20                  25                  30

Val

<210> SEQ ID NO 34
<211> LENGTH: 32
<212> TYPE: PRT
<213> ORGANISM: Homo sapiens
<220> FEATURE:
<221> NAME/KEY: PEPTIDE
<222> LOCATION: (1)..(32)
```

<223> OTHER INFORMATION: Humnan defensin 5, HD-5

<400> SEQUENCE: 34

Ala Thr Cys Tyr Cys Arg His Gly Arg Cys Ala Thr Arg Glu Ser Leu
1               5                   10                  15

Ser Gly Val Cys Glu Ile Ser Gly Arg Leu Tyr Arg Leu Cys Cys Arg
            20                  25                  30

<210> SEQ ID NO 35
<211> LENGTH: 32
<212> TYPE: PRT
<213> ORGANISM: Homo sapiens
<220> FEATURE:
<221> NAME/KEY: PEPTIDE
<222> LOCATION: (1)..(32)
<223> OTHER INFORMATION: Human defensin 6, HD-6

<400> SEQUENCE: 35

Ala Phe Thr Cys His Cys Arg Arg Ser Cys Tyr Ser Thr Glu Tyr Ser
1               5                   10                  15

Tyr Gly Thr Cys Thr Val Met Gly Ile Asn His Arg Phe Cys Cys Leu
            20                  25                  30

<210> SEQ ID NO 36
<211> LENGTH: 68
<212> TYPE: PRT
<213> ORGANISM: Homo sapiens
<220> FEATURE:
<221> NAME/KEY: PEPTIDE
<222> LOCATION: (1)..(68)
<223> OTHER INFORMATION: Human beta defensin, hBD-1

<400> SEQUENCE: 36

Met Arg Thr Ser Tyr Leu Leu Leu Phe Thr Leu Cys Leu Leu Leu Ser
1               5                   10                  15

Glu Met Ala Ser Gly Gly Asn Phe Leu Thr Gly Leu Gly His Arg Ser
            20                  25                  30

Asp His Tyr Asn Cys Val Ser Ser Gly Gly Gln Cys Leu Tyr Ser Ala
        35                  40                  45

Cys Pro Ile Phe Thr Lys Ile Gln Gly Thr Cys Tyr Arg Gly Lys Ala
50                  55                  60

Lys Cys Cys Lys
65

<210> SEQ ID NO 37
<211> LENGTH: 64
<212> TYPE: PRT
<213> ORGANISM: Homo sapiens
<220> FEATURE:
<221> NAME/KEY: PEPTIDE
<222> LOCATION: (1)..(64)
<223> OTHER INFORMATION: Human beta defensin 2, hBD-2

<400> SEQUENCE: 37

Met Arg Val Leu Tyr Leu Leu Phe Ser Phe Leu Phe Ile Phe Leu Met
1               5                   10                  15

Pro Leu Pro Gly Val Phe Gly Gly Ile Gly Asp Pro Val Thr Cys Leu
            20                  25                  30

Lys Ser Gly Ala Ile Cys His Pro Val Phe Cys Pro Arg Arg Tyr Lys
        35                  40                  45

Gln Ile Gly Thr Cys Gly Leu Pro Gly Thr Lys Cys Cys Lys Lys Pro
50                  55                  60

```
<210> SEQ ID NO 38
<211> LENGTH: 67
<212> TYPE: PRT
<213> ORGANISM: Homo sapiens
<220> FEATURE:
<221> NAME/KEY: PEPTIDE
<222> LOCATION: (1)..(67)
<223> OTHER INFORMATION: Human beta defensin 3, hBD-3

<400> SEQUENCE: 38

Met Arg Ile His Tyr Leu Leu Phe Ala Leu Leu Phe Leu Phe Leu Val
1               5                   10                  15

Pro Val Pro Gly His Gly Gly Ile Ile Asn Thr Leu Gln Lys Tyr Tyr
            20                  25                  30

Cys Arg Val Arg Gly Gly Arg Cys Ala Val Leu Ser Cys Leu Pro Lys
            35                  40                  45

Glu Glu Gln Ile Gly Lys Cys Ser Thr Arg Gly Arg Lys Cys Cys Arg
    50                  55                  60

Arg Lys Lys
65
```

COMPOSITIONS AND METHODS FOR TREATMENT OF PROTEASE MEDIATED DISEASE

This application is a continuation of U.S. patent application Ser. No. 16/135,060 filed Apr. 21, 2016, which is a continuation of U.S. patent application Ser. No. 14/491,661 filed Sep. 19, 2014 which is a continuation of U.S. patent application Ser. No. 13/486,548, filed Jun. 1, 2012, and claims the benefit of priority to U.S. Provisional Patent Application No. 61/492,753, filed Jun. 2, 2011.

FIELD OF THE INVENTION

This invention relates to the use of cyclic peptides for modulating cytokine activity, including signaling and inflammatory pathways, in various diseases. More particularly, cyclic peptides possess hereto unknown biological activities, such as inhibition of sheddases and other relevant proteases (metalloproteinases and cysteine proteases), with application across diseases wherein the activities of these proteases relate to pathogenesis of the disease.

BACKGROUND

All publications herein are incorporated by reference to the same extent as if each individual publication or patent application was specifically and individually indicated to be incorporated by reference. The following description includes information that may be useful in understanding the inventive subject matter. It is not an admission that any of the information provided herein is prior art or relevant to the presently claimed inventions, or that any publication specifically or implicitly referenced is prior art.

The cyclic peptides described herein are recently discovered therapeutic agents targeting pro-inflammatory enzymatic pathways of known clinical significance, such as tumor necrosis factor alpha (TNF-α)-converting enzyme ("TACE", also known as ADAM17) and other metalloenzymes (e.g., sheddases and matrix metalloproteinases ("MMPs")) that are implicated in pathologic inflammation, tissue degradation, and the mobilization of growth factors that promote cancer cell proliferation.

Metalloproteinases regulate many biological processes, ranging from developmental programming, response to tissue injury or infection, scar remodeling, and stimulation of cell division (3). Regulation of metalloproteinase activity is crucial for cellular and tissue homeostasis. A number of disease states are associated with over-expression of metalloenzyme activities. For example, the joints affected by rheumatoid and other forms of arthritis have elevated levels of MMPs as well as TNF-α, which is released from the cell surface of pro-TNF-α expressing cells by TACE (7, 8, 13, 16). Blockade of TNF-α with monoclonal antibodies has proven to be effective in the treatment of rheumatoid arthritis (RA) in a significant fraction of patients with RA who are unresponsive to first line drugs such as low dose methotrexate. Because the blockade of TNF-α for RA is not effective in all cases, and because there are serious side effects associated with TNF-α blockers in a subset of patients, there are continuing efforts to develop alternative anti-inflammatory strategies. In this regard, numerous pharmaceutical companies have focused drug development programs on the discovery of TACE inhibitors (17) but none have been approved by the FDA.

Theta defensins (θ-defensins) are naturally occurring cyclic peptides expressed in tissues of rhesus monkeys, baboons, and other Old World monkeys. They are not expressed in humans or other hominids. Naturally occurring θ-defensins are composed of a ring of 18 amino acids stabilized by three disulfide bonds that are conserved among all known θ-defensins (9, 21-23, 25). Like other defensins, θ-defensins were originally discovered based on the antimicrobial properties of the peptides. However, the inventors have discovered a second, hereto unknown property of θ-defensins, as potent anti-inflammatory factors. As described further herein, natural and modified structures of θ-defensins are capable of down regulating inflammation both ex vivo and in vivo. Most importantly, it was discovered that θ-defensins and peptides derived from the structure of θ-defensins (e.g., cyclic peptides), are capable of inhibiting TACE, a key factor in TNF-α inflammation. This totally novel discovery that θ-defensins are natural TACE inhibitors now provides a vital source for molecules capable of regulating inflammation via endogenous cytokine-related pathways existing in a subject. These peptides are the only known natural product expressed in animals that is a soluble regulator of TACE. Thus, cyclic peptides can be used as therapeutics across a variety of disease states or conditions, such as autoimmune and other inflammatory diseases, that result from dysfunctional cytokine activity, and a variety of inflammatory diseases and/or conditions in humans may be due to the loss of θ-defensin expression during primate evolution.

Further, factors such as TACE are members of a broader class of molecules known as sheddases, which possess biological activity of cleaving extracellular protein domains. This cleavage activity has provided a therapeutic pathway for potentiating the efficacy of certain treatments, such as trastuzumab (Herceptin) by inhibition of sheddase ADAM10, for use in breast cancer. Typically, ADAM10 sheddase cleavage of Her2 leads to a Her2 fragment possessing constitutive kinase activity with ligand-independent growth and survival signals to proliferating cells. However, the deleterious effects of this process can be stymied through sheddase inhibition. Thus, cyclic peptides possessing sheddase inhibitory activity provide therapeutic approaches for an even wider variety of diseases and/or conditions, including those wherein changes in metalloproteinase structure, expression, and/or function, relates to pathogenesis of the disease and/or condition.

For over a dozen years, pharmaceutical companies have sought to develop TACE inhibitors (14, 17). While several small molecules (mostly hydroxamates) were shown to be effective in animal models of RA, none of these compounds have been approved due to unacceptable toxicities in humans (14, 17). Indeed all of the existing TNF antagonists have black box warnings, the sternest warning by the U.S. Food and Drug Administration (FDA) that a medication can carry and still remain on the market in the United States.

Therefore, the advent of a non-toxic TACE inhibitor that is efficacious in a disease such as RA would be a valuable addition to the therapeutic approaches to RA, related autoimmune and inflammatory diseases, as well as other diseases involving metalloproteinase activity, such as cancer. In more general terms, there is still a need for medicaments that treat inflammatory and inflammation-related conditions, especially chronic inflammatory conditions, as well as methods of manufacturing, marketing and administering such medicaments.

SUMMARY OF THE INVENTION

The inventive subject matter provides apparatus, systems and methods in which a drug composition that includes a θ-defensin, analog or derivative thereof is researched and marketed to treat an inflammatory condition.

As of the date of this filing, preferred drug compositions include at least one of RTD-1-27, RTD-1-28 and RTD-1-29.

Contemplated in the research aspect of the inventive subject matter are toxicity, efficacy and dose-response studies. Any of such studies can be conducted directly by a pharmaceutical or other company in its own laboratories, or indirectly through a subsidiary or even an unrelated company, all of which should be understood herein as being included in the concept of determining efficacy of the drug composition.

The anti-inflammatory effect(s) contemplated herein should be interpreted to broadly include all clinically relevant inhibition of inflammation-related compounds, including for example, inhibition of tumor necrosis factor alpha (TNF-α)-converting enzyme (TACE), Cathepsin C, or other proinflammatory proteases, the ADAMs family of metalloproteases and other sheddases.

The step of providing the drug composition to the marketplace should be interpreted herein as manufacturing, or having manufactured, or supervising, controlling or in any other manner directing the manufacturing of, a commercial quantity of the drug composition. Contemplated minimal commercial quantities include a total of 1 kilogram, 10 kilograms, 100 kilograms, and 1000 kilograms, during any given one-year period in one or more production facilities.

One interesting aspect of contemplated θ-defensin, analog or derivatives thereof is that many of these compounds are highly stable against acids and proteases, and could be administered in an oral formulation.

At least in part because the contemplated therapeutic compositions can affect TACE and/or sheddases, it is contemplated that many different inflammatory conditions can be treated, including for example, rheumatoid arthritis, inflammatory bowel disease, and other chronic inflammatory diseases, autoimmune diseases, acute bactermia, sepsis, cystic fibrosis, cancer, Alzheimer's, osteoarthritis, inflammation-related neurodegenerative and other inflammation-related diseases. It is especially contemplated that methods and compositions contemplated herein could be advantageously marketed to treat persons who are non-responders to an anti-TNF-α treatment.

Also contemplated are medicaments and methods of manufacturing medicaments for administration to a human or non-human animal, wherein the medicament includes at least one of a novel θ-defensin, analog or derivative thereof disclosed herein or in a priority application that is marketed to treat an inflammatory condition. Of particular interest are RTD-1-27, RTD-1-28 and RTD-1-29.

Various objects, features, aspects and advantages of the inventive subject matter will become more apparent from the following detailed description of preferred embodiments

DETAILED DESCRIPTION

Figure 1:
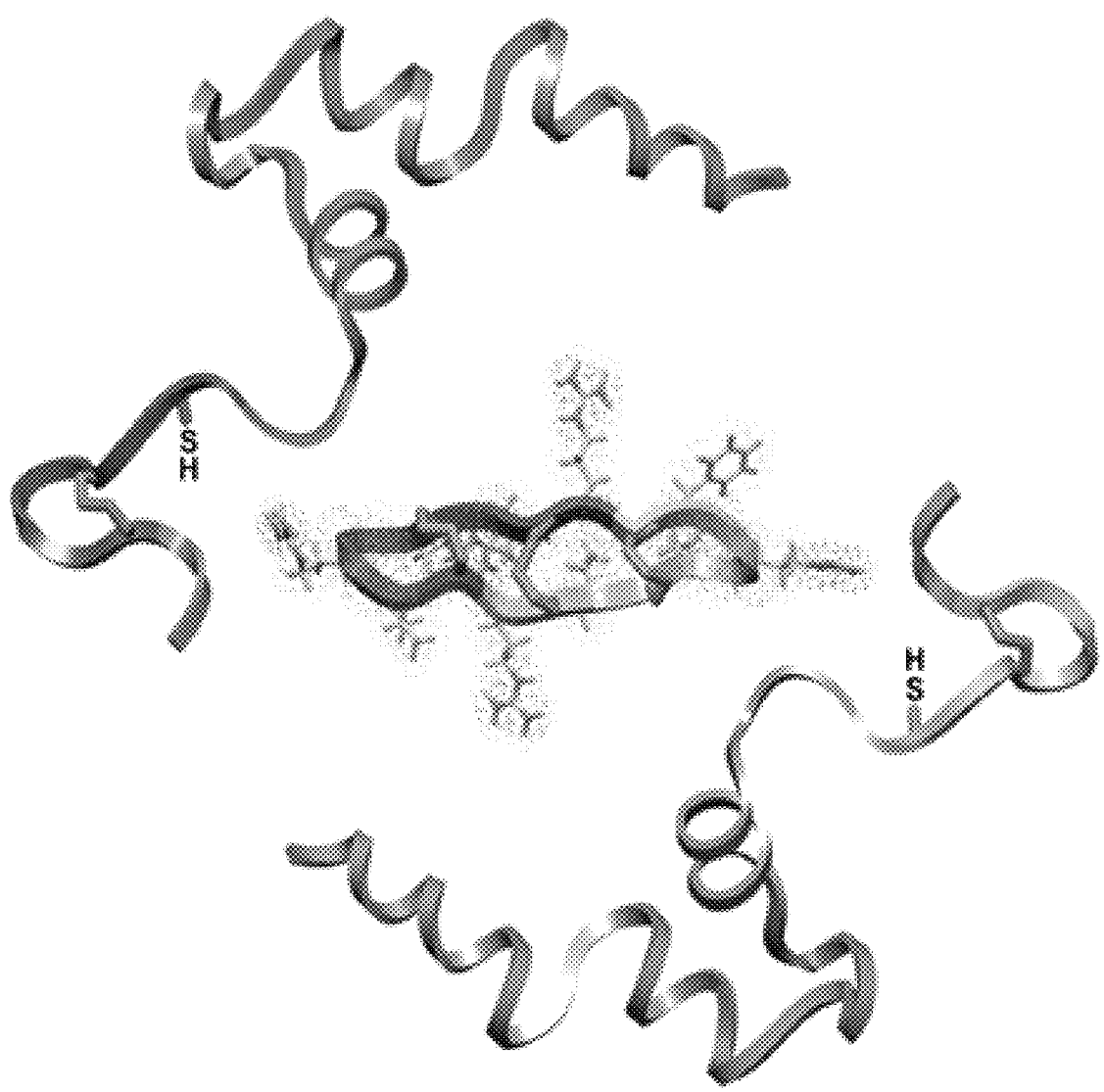
FIG. 1. θ-defensin biosynthesis and structure. Substituent nonapeptides (color coded) are excised and spliced to produce the mature peptide RTD-1 (from (21)).

All references cited herein are incorporated by reference in their entirety as though fully set forth. Unless defined otherwise, technical and scientific terms used herein have the same meaning as commonly understood by one of ordinary skill in the art to which the inventive subject matter belongs. Singleton et al., *Dictionary of Microbiology and Molecular Biology* 3$^{rd}$ ed., J. Wiley & Sons (New York, NY 2001); March, *Advanced Organic Chemistry Reactions, Mechanisms and Structure* 5$^{th}$ ed., J. Wiley & Sons (New York, NY 2001); and Sambrook and Russel, *Molecular Cloning: A Laboratory Manual* 3rd ed., Cold Spring Harbor Laboratory Press (Cold Spring Harbor, NY 2001); provide one skilled in the art with a general guide to many of the terms used in the present application.

One skilled in the art will recognize many methods and materials similar or equivalent to those described herein, which could be used in the practice of the claimed inventions. Indeed, the inventive subject matter should not be interpreted as being limited to the methods and materials described. For present purposes, the following terms are defined below.

Unless the context dictates the contrary, all ranges set forth herein should be interpreted as being inclusive of their endpoints, and open-ended ranges should be interpreted to include commercially practical values. Similarly, all lists of values should be considered as inclusive of intermediate values unless the context indicates the contrary.

As used herein the terms "Theta-defensins" or "θ-defensins" include members of the θ-defensin family of defensin proteins as found in various primate species, such as Old World monkeys and apes (examples being the rhesus monkey, olive baboon, siamang gibbon and orangutan), wherein θ-defensins precursors are expressed transcriptionally and processed via post-translational modification into θ-defensin. This further includes pseudogenes found in Great Apes (examples being human, chimpanzees, bonobos, and gorillas), wherein genetic modification of θ-defensin pseudogenes may be altered according to techniques readily known in the art, to allow expression of θ-defensin proteins in mammalian cells. This also includes θ-defensin proteins that may be identified in the same or different species, according to techniques readily known in the art, such as computer modeling techniques describing sequence homology or conserved structure in a comparison window of nucleic acid and/or amino acid sequences, or selective hybridization techniques using nucleic acid probes to identify homologous θ-defensins. θ-defensins may be isolated from endogenous sources, produced in autologous or heterologous cell lines, produced via peptide synthesis, or according to any available method known to one of skill in the art. Examples of θ-defensins include RTD-1, RTD-2, RTD-3, RTD-4, RTD-5, RTD-6, BTD-1, BTD-2, BTD-3, BTD-4, BTD-5, BTD-6, BTD-7, BTD-8, BTD-9, BTD-10 or HTDp.

"Sheddase", as used herein, includes enzymatic proteins that cleave extracellular portions of transmembrane proteins. Examples include members of the disintegrin and metalloproteinase family (ADAM) of proteins, aspartic protease (BACE) family of proteins, among others. Examples of ADAM proteins that are sheddases include ADAM2, ADAM7, ADAM8, ADAM9, ADAM10, ADAM11, ADAM12, ADAM15, ADAM17, ADAM18 (also known as ADAM27), ADAM19, ADAM20, ADAM21 (also known as ADAM31), ADAM22, ADAM23, ADAM28, ADAM29, ADAM30, and ADAM33.

The term "analog", as applied to θ-defensins herein, are polypeptides and peptides that contain a core structure derived from a defensin, such as θ-defensin, that is capable of modulating cytokine activity, inhibiting proteolytic sheddase activity, altering enzyme function related to cell surface receptors, and/or possesses anti-microbial activity. Examples include cyclic peptides containing one, two, three, four, or more disulfide bonds across multiple cysteine residues or substantially similar substitutes, wherein the analog can range in length from 8-24 amino acids, and contains a net positive charge.

Defensins are small cysteine-rich cationic proteins that are highly evolutionarily conserved, as found in vertebrates, invertebrates, as well as plants. These proteins possess biological activity against a wide spectrum of organisms such as bacteria, fungi and many enveloped and non-enveloped viruses. Generally, defensins consist of 18-45 amino acids including 6 (in vertebrates) to 8 conserved cysteine residues. Various immune cells, such as neutrophil granulocytes and almost all epithelial cells, contain these peptides as host cells, with a key function of killing phagocytized or extracellular microorganisms. Many defensins function by binding to the microbial cell membrane, and, once embedded, form pore-like membrane defects that allow efflux of essential ions and nutrients to destroy microbe integrity. However, as further described herein, certain members of defensin proteins, including θ-defensins, also act through modulation of host cell immune function. This includes cytokine related inflammatory pathways such as TNF-α.

Defensins, Generally. Defensins are cationic, tridisulfide-containing antimicrobial peptides that are produced by leukocytes and various epithelia. They are subdivided into the α-, β-, θ-defensin subfamilies, which are distinguished by peptide size and different disulfide motifs. In humans, four α-defensins (HNP-1 to HNP-4) have been isolated from neutrophils and two enteric α-defensins (HD-5 and HD-6) are expressed by Paneth cells in crypts of the small intestine. The expression of HD-5 has also been detected in the female urogenital tract. Three human β-defensins (hBD-1 to hBD-3) have been isolated from epithelial and nonepithelial cell types of various organs, and the expression of several others has been deduced by cDNA analysis or from analysis of the human genome. Numerous lines of evidence suggest that defensins provide an antimicrobial effector function in skin, the respiratory epithelium, the urogenital tract, and various leukocytes (i.e., neutrophils, monocytes, and NK cells). Furthermore, defensins activate cells involved in both the innate and the adaptive immune responses, suggesting that they operate within and link two branches of immunity.

Macrocyclic θ-Defensins. θ-defensins are cyclic octadecapeptides formed by the posttranslational splicing of two nonapeptides derived from 76-amino-acid α-defensin-related precursors. Humans do not express θ-defensin peptides since the expression of θ-defensins ceased near the time that orangutans emerged in evolution due to a mutation that introduced a premature stop codon in the peptide precursor.

θ-defensins can be bio-synthesized using head-to-tail splicing of two 9-amino-acid sequences derived from θ-defensin precursors. θ-defensins were first identified in neutrophils and monocytes of the rhesus monkey, with a subsequent phylogenetic survey revealing the existence of θ-defensin genes in other Old World monkeys and two apes (the siamang and orangutan), but the existence of θ-defensins in New World monkeys or prosimians has not yet been reported. Humans, chimpanzees, bonobos, and gorillas express θ-defensin pseudogenes in which the precursor mRNA contains a mutation producing a stop codon in the signal sequence, thus preventing translation of the θ-defensin precursor. Rhesus θ-defensin-1 (RTD-1) is produced from the heterodimeric splicing of two θ-defensin precursors, proRTD1a and proRTD1b. Homodimeric excision/ligation reactions involving proRTD1a and proRTD1b were revealed by the isolation of RTD-2 and RTD-3. RTD-1, -2, and -3 have potent microbicidal activities against bacteria and fungi and have been known to possess antiviral activities against human immunodeficiency virus type 1 (HIV-1) and herpes simplex virus (HSV).

We have created synthetic θ-defensin designs based on the sequence of a natural θ-defensin that possess antibacterial and antiviral activities. In addition, θ-defensins are reported to bind and inactivate lethal toxin from *Bacillus anthracis*. θ-defensins are microbicidal in the presence of physiological concentrations of salt, divalent cations, and serum. In contrast, the antimicrobial activities of α- and β-defensins are markedly reduced in the presence of salt and divalent cations. Acyclic RTD-1 is inactive against *Staphylococcus aureus* in physiologic saline, whereas the natural cyclic form of the peptide retained potent killing activity under these conditions. These data indicate that the cyclic backbone structure of θ-defensins confers salt insensitivity, while providing a stable molecule capable of retaining potent biologically activity under physiologically relevant conditions.

Antimicrobial Activity of θ-Defensins. The archetypal θ-defensin peptide is rhesus θ-defensin-1 (RTD-1), an 18-amino acid macrocyclic peptide (22). As described, the mature peptide is produced by a unique process whereby two 9-amino acid peptides, derived from truncated α-defensin-like precursors, are spliced head-to-tail to form a macrocyclic molecule stabilized by three disulfides (FIG. 1). The biosynthetic pathway that gives rise to the mature macrocyclic θ-defensin is novel. Rhesus monkeys (22, 23, 25) and Olive baboons (9) express 3 and 4 θ-defensin precursors, respectively. Each precursor donates a unique nonapeptide that is paired with an identical (homodimeric splicing) or different (heterodimeric splicing) nonapeptide in all binary combinations. This enables the production of 6 unique macaque θ-defensins and 10 baboon θ-defensins. The inventors have isolated all six of the predicted macaque peptides (23) and has isolated seven of those predicted in baboon (9).

Similar to other defensins, such as α-defensins, θ-defensins are packaged in the primary granules of macaque and baboon neutrophils and are also expressed in monocytes (23). As microbes are phagocytosed by neutrophils, monocytes, and macrophages, defensins are mobilized to the phagosome where they participate in intracellular killing as microbicides. θ-defensins are microbicidal at submicromolar concentrations against gram positive bacteria, fungi, (9, 22, 25) and inhibit cellular uptake of HIV-1 (5, 6, 27, 28). Using a specific neutralizing antibody, the inventors have demonstrated that θ-defensins are responsible for the majority of the granule-derived antimicrobial activities of macaque neutrophils against *S. aureus, E. coli*, and *C. albicans* in vitro (23). Moreover, θ-defensins were shown to be responsible for the superior killing activities of macaque PMN granule extracts compared to extracts from human neutrophil granules (23). During systemic inflammation (e.g., sepsis) in humans, α-defensins are released in a directed and/or accidental fashion to the extracellular space (2, 18). Baboon θ-defensins (22) are similarly released into the serum of bacteremic animals. Further, extracellular θ-defensins appear to possess the capacity to modulate inflammation via anti-inflammatory mechanisms that are operative in species ranging from rodents to humans, as further described herein. Thus, θ-defensins and peptides derived from the structure of θ-defensins, represent an important class of immune function modulators.

TNF-α and Inflammation. Tumor necrosis factor alpha ("TNF-α", also known as cachexin or cachectin) is a cytokine involved in systemic inflammation and is a member of a group of cytokines that stimulate the acute phase reaction.

TNF-α plays a key role in the regulation of immune cells, including induction of apoptotic cell death, promotion of inflammation, inhibition of tumorigenesis and viral replication. Given the wide ranging effects of TNF-α activity, it is unsurprising to find that dysregulation of TNF-α expression, production and signaling, has been implicated in a variety of human diseases, including rheumatoid arthritis, Alzheimer's disease, tuberculosis, Crohn's disease, among many others.

TNF-α signaling is first produced as a 26 kDa, 212-amino acid-long type II transmembrane protein that becomes inserted into the cell membrane during maturation. At the cell surface, membrane-bound TNF-α ("pro-TNF-α") is biologically active, and is able to induce immune responses via juxtacrine intercellular signaling. However, pro-TNF-α can undergo a proteolytic cleavage at its Ala76-Val77 amide bond by the metalloproteinase TNF-α converting enzyme ("TACE", also known as ADAM17). From this membrane-integrated form, the soluble 17 kDa extracellular domain (ectodomain), commonly known as TNF-α, is released which is of pivotal importance in paracrine signaling.

Generally, existing therapeutic strategies targeting TNF-α activity have focused on providing antibodies against soluble and/or transmembrane bound forms of TNF-α to prevent receptor binding, or creating soluble hybrid fusion receptors to neutralize circulating TNF-α levels. Despite the important benefits of these therapeutic approaches, nearly ⅓ of patients do not respond to any form of anti-TNF-α therapy, while several adverse effects have been reported, including immunogenicity, infections, delayed hypersensitivity-type reactions and autoimmune diseases such as drug-induced lupus and demyelination.

TACE and Sheddase Activity. As described, a key step in TNF-α signaling activity is liberation of the membrane bound form of the protein into a soluble form of circulating TNF-α, as catalyzed by TACE, a process known as "shedding". TACE, a 70-kDa protein composed of 824 amino acids, belongs to the ADAM protein family of disintegrins and metalloproteinases (A Disintegrin And Metalloproteinase). Members of the ADAM protein family possess both evolutionarily conserved structures and functional capability of cleavage and release of a soluble ectodomain from membrane-bound pro-proteins. Given TNF-α's role as a potent and pivotal mediator in the inflammatory process, cyclic peptides that function as TACE inhibitors would offer a vital alternative to current anti-TNF-α agents, such as antibody or soluble receptor-based compositions.

Further, TNF-α and TACE represent only two of several potential therapeutic targets for cyclic peptide therapeutic activity, given the breadth and diversity of "shedding" activity across several different proteins, and as implicated in many different disease states and/or conditions. TACE and other ADAM family molecules constitute most members of the larger family of "sheddases". However, other sheddases include members of the aspartic protease (BACE) protein families. Beyond the breadth of sheddase types, the function of sheddase activity varies from signaling activation via cleavage of a transmembrane protein receptor ectodomain (e.g., Her2), or following agonist binding to the receptor to allow the liberated agonist to further stimulate another receptor (e.g., EGFR). Due to this vital role in enabling and propagating signaling function, inhibition of sheddase activity provides an important therapeutic strategy to open new therapeutic avenues, and also to potentiate efficacy of existing drug treatments. For example, ADAM10 sheddase cleavage of Her2 leads to a Her2 fragment possessing constitutive kinase activity with ligand-independent growth and survival signals to proliferating cells. The deleterious effects of this process can be stymied through trastuzumab (herceptin) administration and inhibition of ADAM 10 sheddase activity (30, 31). As a result, cyclic peptides may be used for limiting harmful cytokine activity as related to immune function, while opening up even wider therapeutic opportunities for diseases such as cancer, or other diseases and/or conditions involving sheddase dysfunction. This aspect of θ-defensins, as possessing an endogenous sheddase inhibitory activity, may account for a number of autoimmune, inflammatory diseases and other disease conditions in human subjects, due to the loss of θ-defensin expression during primate evolution. Thus, θ-defensins and cyclic peptides derived from the structure of various θ-defensins, can be used as compatible therapeutics in human subjects afflicted with disease and conditions associated with metalloproteinase dysregulation.

In various embodiments, the inventive subject matter provides cyclic peptides. In one class of embodiments, the cyclic peptide is a defensin, analog or derivative thereof. In another class of embodiments, the cyclic peptide is an α-defensin, β-defensin, θ-defensin, analog or derivative thereof. In another class of embodiments, the cyclic peptide is a θ-defensin, analog or derivative thereof.

In another class of embodiments, the θ-defensin is endogenously expressed in a primate. In another class of embodiments, the θ-defensin is endogenously expressed in a rhesus monkey. In another class of embodiments, the θ-defensin is RTD-1, RTD-2, RTD-3, RTD-4, RTD-5, or RTD-6. In another class of embodiments, the θ-defensin is endogenously expressed in an olive baboon. In another class of embodiments, the θ-defensin is BTD-1, BTD-2, BTD-3, BTD-4, BTD-5, BTD-6, BTD-7, BTD-8, BTD-9 or BTD-10. In another class of embodiments, the θ-defensin is endogenously expressed in a human. In another class of embodiments, the θ-defensin is human θ-defensin pseudogene (HTDp). In another class of embodiments, the θ-defensin is expressed in a siamang or orangutan.

In another class of embodiments, the θ-defensin is isolated from a mammal. In another class of embodiments, the θ-defensin is isolated from a primate. In another class of embodiments, the θ-defensin is isolated from a human. In another class of embodiments, the θ-defensin is purified from a biological sample obtained from a mammal. In another class of embodiments, the θ-defensin is purified from a biological sample obtained from a primate. In another class of embodiments, the θ-defensin is purified from a biological sample obtained from a human.

In another class of embodiments, the cyclic peptide is 8, 9, 10, 11, 12, 13, 14, 15, 16, 17, 18, 19, 20, 21, 22, 23, or 24 amino acids in length. In another class of embodiments, the cyclic peptide is over 24 amino acids in length. In a particular embodiment, the cyclic peptide is 14 amino acids in length. In another class of embodiments, the cyclic peptide contains at least 2 cysteine residues forming one disulfide bond. In another class of embodiments, the cyclic peptide contains 4 cysteine residues forming 2 disulfide bonds. In another class of embodiments, the cyclic peptide contains 6 cysteine residues forming 3 disulfide bonds. In another class of embodiments, the cyclic peptide includes a synthetic amino acid. In another class of embodiments, the cyclic peptide has a net positive charge. In another class of embodiments, cyclic peptide may be encoded by a polynucleotide possessing less than about 20%, 25%, 30%, 35%, 40%, 45%, 50%, 55%, 60%, 65%, 70%, 75%, 80%, 85% or more percentage identity to SEQ. NO. 1, SEQ. NO. 2, SEQ. NO. 3, SEQ. NO. 4, SEQ. NO. 5, SEQ. NO. 6, and/or SEQ. NO. 7. One of ordinary skill in the art can establish percentage identity according to methods known in the art, including establishing a comparison window between a reference sequence and a second polynucleotide sequence, to establish the degree of percentage identity.

In another class of embodiments, the cyclic peptide modulates inflammation. In another class of embodiments, the cyclic peptide modulates the activity of a cytokine and/or chemokine. In another class of embodiments, the cyclic peptide modulates the activity of TNF-α. In another class of embodiments, the cyclic peptide modulates the activity of TNF-α through competitive inhibition with a member of the disintegrin and metalloproteinase family. In another class of embodiments, the member of the disintegrin and metalloproteinase family is a sheddase. In another class of embodiments, the sheddase is TACE. In another class of embodiments, the sheddase is ADAM10. In another class of embodiments, the cyclic peptide is capable of modulating proteolytic enzyme activity. In another class of embodiments, the cyclic peptide is capable of anti-microbial killing.

In various embodiments, the inventive subject matter provides methods of treating an inflammatory disease and/or condition using a cyclic peptide including the steps of providing a quantity of a cyclic peptide, administering the quantity of the cyclic peptide to a subject in need of treatment for an inflammatory disease and/or condition, wherein the cyclic peptide is capable of modulating inflammation, thereby treating the subject. In another class of embodiments, the cyclic peptide is a θ-defensin, analog or derivative thereof. In another class of embodiments, the θ-defensin is RTD-1, RTD-2, RTD-3, RTD-4, RTD-5, RTD-6, BTD-1, BTD-2, BTD-3, BTD-4, BTD-5, BTD-6, BTD-7, BTD-8, BTD-9 or BTD-10. In another class of embodiments, the cyclic peptide is 8, 9, 10, 11, 12, 13, 14, 15, 16, 17, 18, 19, 20, 21, 22, 23, or 24 amino acids in length. In another class of embodiments, the cyclic peptide is over 24 amino acids in length. In another class of embodiments, the cyclic peptide is 14 amino acids in length. In another class of embodiments, the cyclic peptide contains at least 2 cysteine residues forming one disulfide bond. In another class of embodiments, the cyclic peptide contains at least 4 cysteine residues forming two or more disulfide bonds. In another class of embodiments, the quantity of the cyclic peptide administered is a therapeutically effective amount of the cyclic peptide. In another class of embodiments, the subject is a mammal. In another class of embodiments, the subject is a human.

In various embodiments, the inflammatory disease and/or condition is acute or chronic inflammation or an autoimmune disease. In another class of embodiments, the inflammatory disease and/or condition relates to the activity of a cytokine or chemokine In another class of embodiments, the inflammatory disease and/or condition relates to the activity of TNF-α. In another class of embodiments, the inflammatory disease and/or condition is rheumatoid arthritis, ankylosing spondylitis, inflammatory bowel disease, ulcerative colitis, autistic enterocolitis, psoriasis, psoriatic arthritis, Crohn's disease, Behcet's disease, lupus, hidradenitis suppurativa, refractory asthma, colitis, dermatitis, diverticulitis, hepatitis, nephritis, Parkinson's disease, Alzheimer's disease, Huntington's disease, congestive heart disease, atherosclerosis, uveitis, and allergy.

In various embodiments, the inventive subject matter further provides a method of enhancing efficacy of a treatment for an inflammatory disease and/or condition using a cyclic peptide, including the steps of providing a quantity of a cyclic peptide, administering the quantity of the cyclic peptide to a subject receiving treatment for an inflammatory disease and/or condition, wherein the cyclic peptide is capable of enhancing the efficacy of the treatment for an inflammatory disease and/or condition, thereby enhancing efficacy of the treatment. In another class of embodiments, the cyclic peptide is administered simultaneously with a composition capable of treating an inflammatory disease and/or condition. In another class of embodiments, the cyclic peptide is administered sequentially, before or after administration, of a composition capable of treating an inflammatory disease and/or condition. In another class of embodiments, the subject is a mammal. In another class of embodiments, the subject is a human.

In various embodiments, the inventive subject matter further provides a method of treating a disease and/or condition in a subject using a cyclic peptide. In another class of embodiments, the disease and/or condition is cancer or a neurodegenerative disease. In various embodiments, the inventive subject matter further provides a method of enhancing efficacy of a treatment for a disease and/or condition using a cyclic peptide. In another class of embodiments, the cyclic peptide is administered simultaneously with a composition capable of treating a disease and/or condition. In another class of embodiments, the cyclic peptide is administered sequentially, before or after administration, of a composition capable of treating a disease and/or condition. In preferred embodiments the subject is a mammal, and in especially preferred embodiments the subject is a human.

In various embodiments, the inventive subject matter further provides a pharmaceutical composition. In another class of embodiments, the pharmaceutical composition comprises a cyclic peptide and a pharmaceutically acceptable carrier. In another class of embodiments, the cyclic peptide is a θ-defensin, analog or derivative thereof. In another class of embodiments, the θ-defensin is RTD-1, RTD-2, RTD-3, RTD-4, RTD-5, RTD-6, BTD-1, BTD-2, BTD-3, BTD-4, BTD-5, BTD-6, BTD-7, BTD-8, BTD-9 or BTD-10. In another class of embodiments, the cyclic peptide is 8, 9, 10, 11, 12, 13, 14, 15, 16, 17, 18, 19, 20, 21, 22, 23, or 24 amino acids in length. In another class of embodiments, the cyclic peptide is 14 amino acids in length. In another class of embodiments, the cyclic peptide is over 24 amino acids in length. In another class of embodiments, the cyclic peptide contains at least 2 cysteine residues forming one disulfide bond. In another class of embodiments, the cyclic peptide contains at least 4 cysteine residues forming two or more disulfide bonds. In another class of embodiments, the cyclic peptide in the pharmaceutical composition includes a therapeutically effective amount of the cyclin peptide. In another class of embodiments, pharmaceutical composition comprises one or more cyclic peptides and a pharmaceutically acceptable carrier.

In various embodiments, the inventive subject matter further provides a method of manufacturing a cyclic peptide. In another class of embodiments, the method of manufacturing includes the steps of providing one or more polynucleotides encoding a cyclic peptide, expressing the one or more polynucleotides in a host cell, and extracting the cyclic peptide from the host cell. In another class of embodiments, the method of manufacturing includes the steps of expressing the one or more polynucleotides in a host cell, and extracting the cyclic peptide from the host cell. In another class of embodiments, the one or more polynucleotides include SEQ. NO. 1, SEQ. NO. 2, and/or SEQ. NO. 3. In another class of embodiments, the one or more polynucleotides include SEQ. NO. 4, SEQ. NO. 5, SEQ. NO. 6, and/or SEQ. NO. 7.

In another class of embodiments, the cyclic peptide is a θ-defensin, analog or derivative thereof. In another class of embodiments, the θ-defensin is RTD-1, RTD-2, RTD-3, RTD-4, RTD-5, RTD-6, BTD-1, BTD-2, BTD-3, BTD-4, BTD-5, BTD-6, BTD-7, BTD-8, BTD-9 or BTD-10. In another class of embodiments, the cyclic peptide is 8, 9, 10, 11, 12, 13, 14, 15, 16, 17, 18, 19, 20, 21, 22, 23, or 24 amino acids in length. In another class of embodiments, the cyclic peptide is 14 amino acids in length. In another class of embodiments, the cyclic peptide contains at least 2 cysteine residues forming one disulfide bond. In another class of embodiments, the cyclic peptide contains at least 4 cysteine residues forming two or more disulfide bonds. In another embodiment, the method of manufacturing include the steps of peptide synthesis using liquid-phase synthesis or solid-phase synthesis. In another class of embodiments, the solid-phase synthesis is Fmoc or BOC synthesis.

Manufacture of the compositions contemplated herein can be accomplished in any suitable manner, including for example using expression vectors. An ordinarily skilled person can choose a suitable expression vector, and will recognize that there are enormous numbers of choices. Many of these vectors use viral promoters. Many choices of cell lines are suitable for the host cell, including for example, bacteria, yeast, insect cells, and plants.

EXAMPLES

Figure 2:
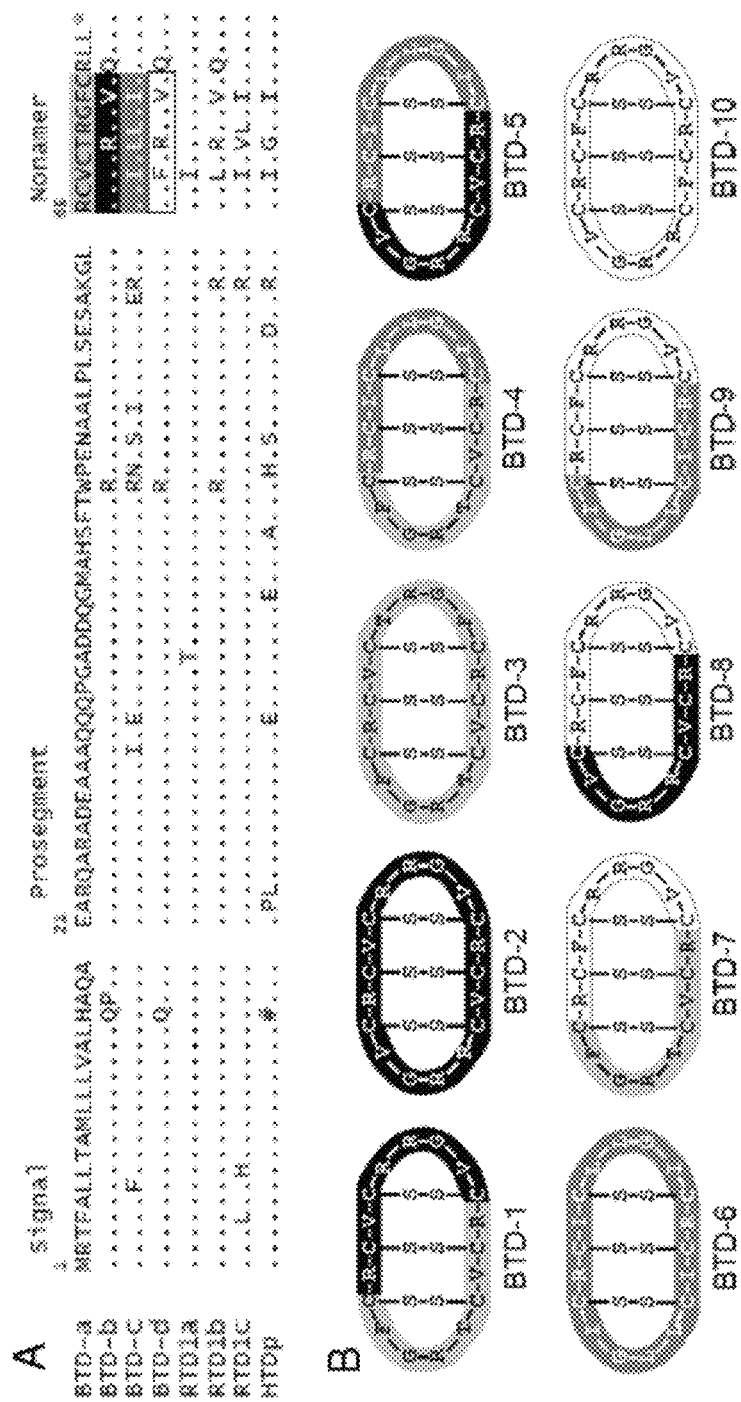
FIG. 2. Alignment of prepro-θ-defensins. A. BTD-a to -d amino acid sequences predicted from cDNA are aligned manually with RTD1a to -c, and human θ-defensin pseudogene (HTDp). Dots in aligned sequences denote amino acids identical to those in BTD-a, the asterisk symbol denotes the position of termination codon, and the # symbol denotes a stop codon that prematurely terminates translation. B. Cyclic structures of 10 deduced BTD peptides derived from cDNA sequences.

Example 1—Unique Properties of Pleiotropic θ-Defensins and Anti-Inflammatory Properties θ-defensins kill *E. coli* cells by generating small pores in the cell envelope that mediates their own uptake (24). In this study, the inventors made the remarkable discovery that, unlike many α- and β-defensins, θ-defensins are non-toxic to host cells (24) and may be administered by various routes to mice (29). In this regard, mice readily tolerate i.v. administration of at least 80 mg/kg doses of three different θ-defensins. The inventors have also administered RTD-1 in escalating i.v. doses (3 mg/kg maximum) to two adult chimpanzees. No clinical toxicity was observed at any point and all clinical chemistry and hematologic laboratory values were within normal limits following all injections. Neither animal produced an antibody to RTD-1, thereby demonstrating a remarkable lack of toxicity and immunogenicity across different mammalian species. Based on these and other data, RTD-1 was tested for efficacy in a mouse model of severe sepsis induced by cecal ligation and puncture (CLP) (12). As shown in FIG. 2, a single injection of RTD-1 (5 mg/kg) markedly reduced death in BALB/c mice when the peptide was administered 4 or 24 h after CLP surgery (P<0.01 at days 4 and 7). Survivors at day 7 were normal clinically to day 15 at which time they were sacrificed. This therapeutic effect of θ-defensins in CLP-sepsis was highly reproducible (N=5 experiments). However, the high degree of efficacy for θ-defensins suggested that the efficacy of RTD-1 in this model was not primarily mediated by an antibiotic effect, since the microbiome in polymicrobial sepsis is enormous. Rather, the potency of the demonstrated therapeutic effect was believed to be further mediated through an anti-inflammatory mechanism. To explore this possibility, the inventors conducted additional experiments, wherein RTD-1 treatment of CLP mice was accompanied by marked reductions in a wide variety of serum proinflammatory cytokines, including TNF-α, IL-6, and MIF.

Others studies have demonstrated that natural (10, 15) or designed (11) AMPs are effective in rodent models of sepsis. In each case, the apparent protective mechanism was binding of bacterial LPS by the peptide, thereby circumventing the interaction with host cell proteins (LPS binding protein) or receptors (TLR-4, CD14). In this regard, nearly all AMPs analyzed have been shown to bind and neutralize LPS, supporting the conclusion that this is the chief mechanism mediating their anti-sepsis activities (19).

However, θ-defensins are less effective in directly neutralizing LPS, being 100-fold less active than polymyxin B in neutralizing endotoxin. Rather, as discussed below, studies demonstrate that θ-defensins possess several functional capabilities, including a primary means of modulating inflammation by interactions with host cells. This finding is consistent with earlier studies in which RTD-1 was evaluated for efficacy in a mouse model of SARS-coronavirus (SARS-CoV) pneumonitis (29). In this study, the inventors discovered that intranasal administration of RTD-1 was 100% effective in preventing death of virally-infected mice. Significantly, RTD-1 was not virucidal against SARS-CoV. However, peptide administration reduced pulmonary inflammation and the expression of several pro-inflammatory cytokines, thereby suggesting that the therapeutic effect was mediated by the anti-inflammatory properties of the RTD-1. Without being bound by any particular theory, the inventors' belief that θ-defensins modulate host responses to pro-inflammatory stimuli was confirmed by further experiments demonstrating that RTD-1 is therapeutically effective in pristane-induced arthritis in the rat (FIG. 9; discussed below) and in collagen-induced arthritis.

Figure 3:
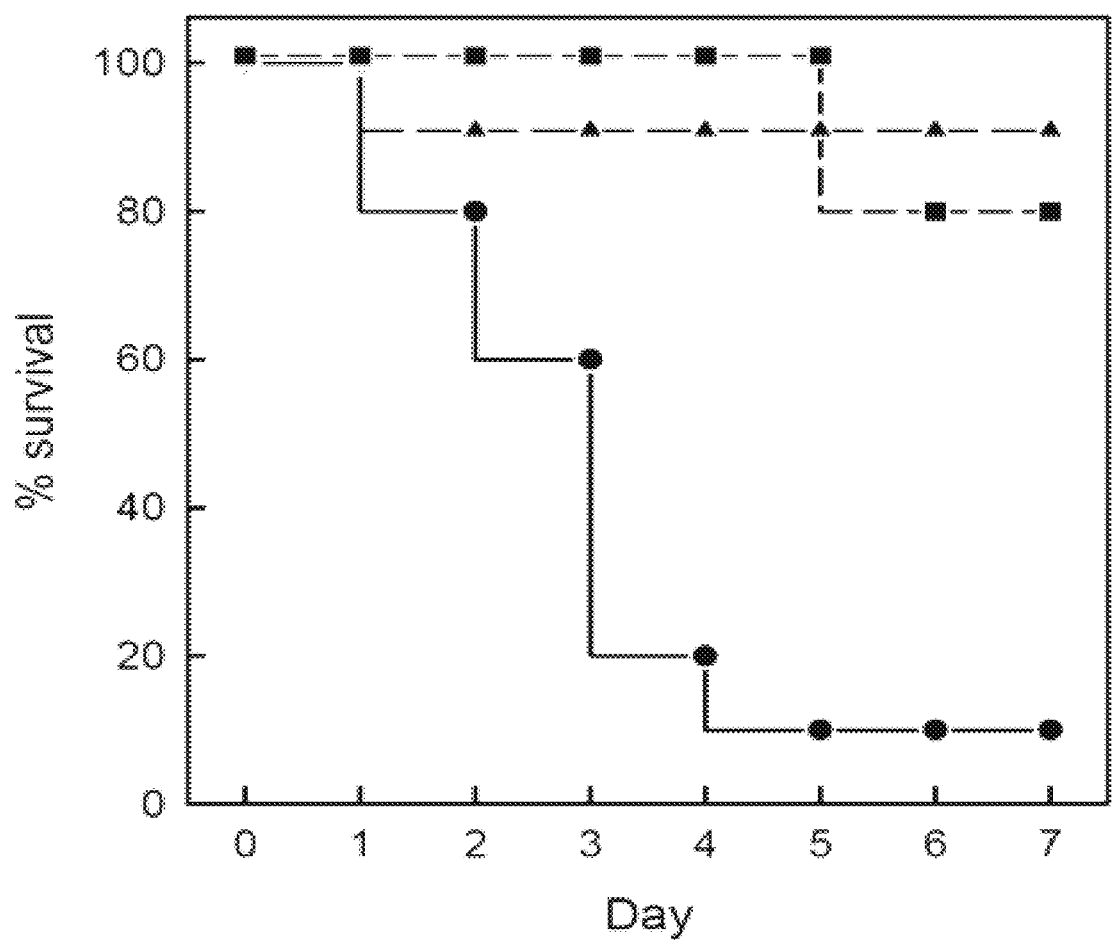
FIG. 3. RTD-1 reduces lethality in mouse polymicrobial sepsis. Adult Balb/c mice received cecal ligation and puncture (CLP) at T=0. Mice received a single 150 μl injection of normal saline (●, n=10) 4 h after CLP or saline containing 5 mg/kg of RTD-1 at 4 h (▲, n=11) or 24 h (■, n=5) after CLP surgery.
Figure 4:
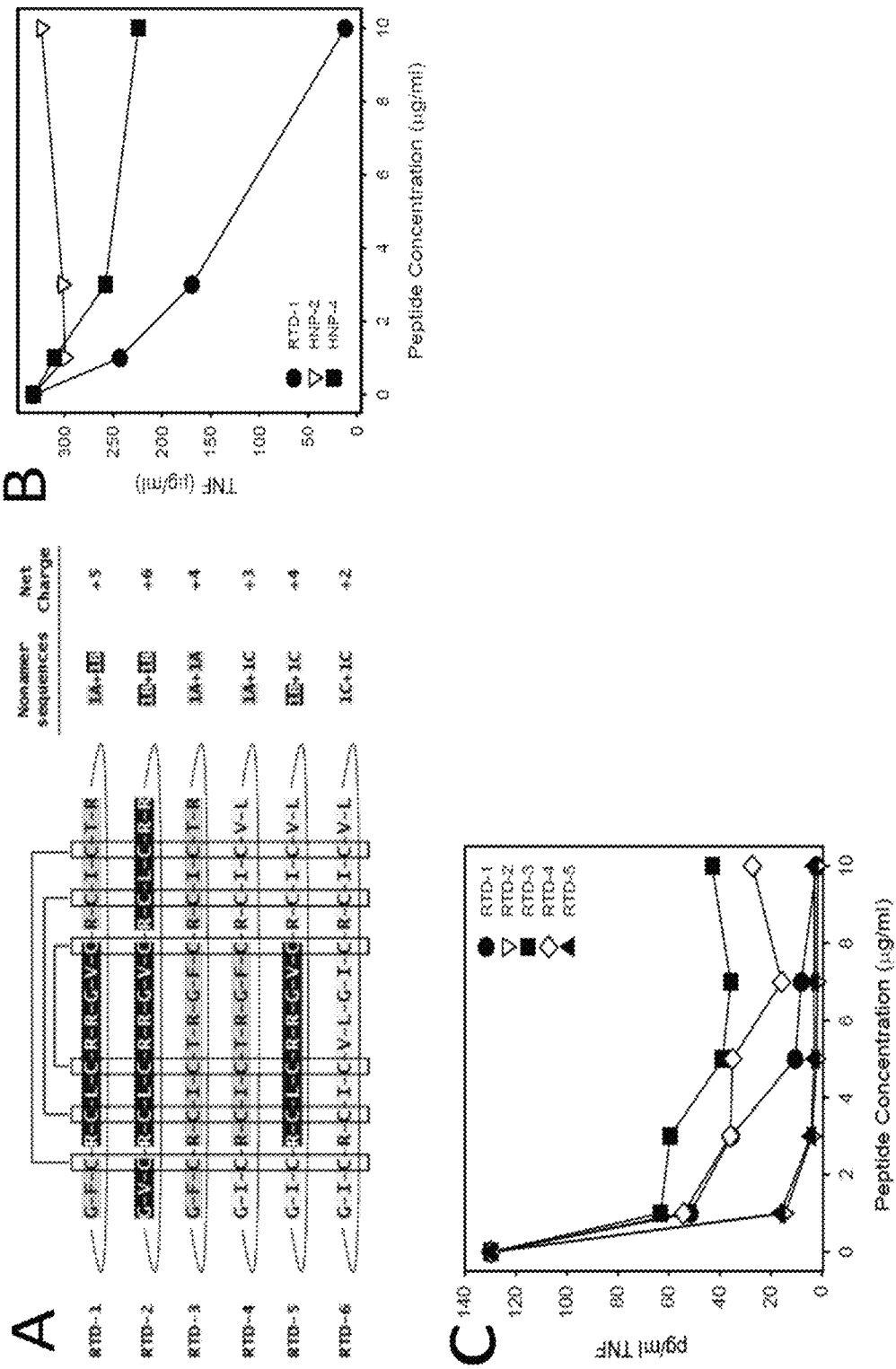
FIG. 4. Anti-TNF activities of θ-defensins. A. Covalent structures of RTD 1-6 (23) with color coding showing derivation of constituent nonapeptides (23). B. Human whole blood (1:10) was incubated with 100 CFU/ml of live $E.\ coli$ for 4 h in the presence of 0-10 μg/ml θ-defensin RTD-1 and two human α-defensins (HNP-2 and HNP-4) and TNF-α was quantified by ELISA. C. RTDs 1-5 were tested for effect on TNF-α release from human whole blood as in panel B; TNF-α was quantified by ELISA. RTD-6, present in only trace quantities in PMNs has not been tested.
Figure 5:
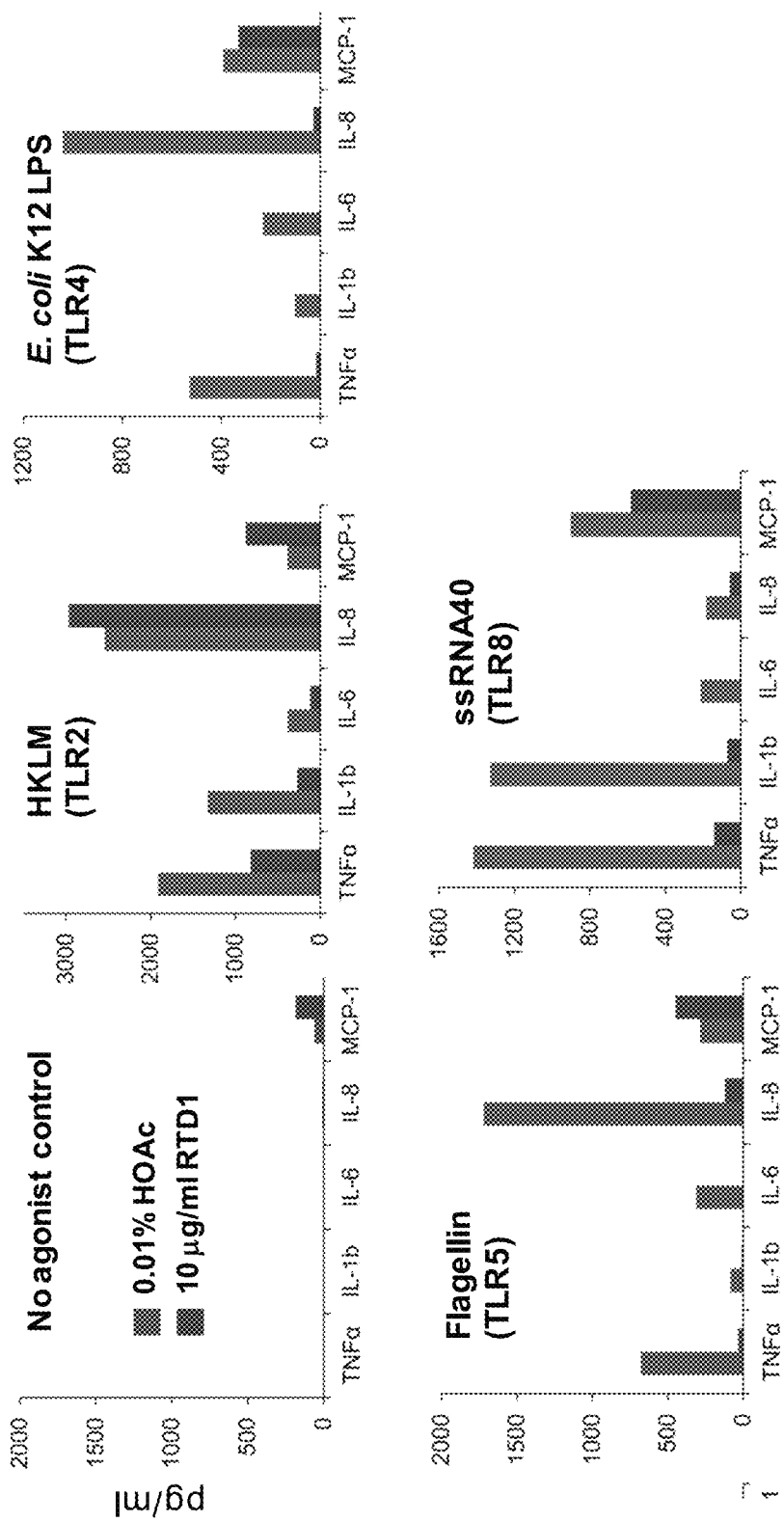
FIG. 5. θ-defensins inhibit pro-inflammatory cytokines/chemokines induced by multiple TLR agonists. Human peripheral blood cells ($5 \times 10^5$ cells/ml) in RPMI 1640+5% human plasma were incubated with 10 μg/ml of RTD-1 alone (No agonist control) or peptide solvent (0.01% HOAc) or simultaneously with TLR agonists for 4 h at 37° C. in 5% CO2 with gentle agitation. Supernatants were harvested by centrifugation and cytokine/chemokine levels were quantified by Luminex xMAP analysis using a Milliplex cytokine/chemokine panel. Agonists: TLR2—$1 \times 10^8$ heat killed $L.\ monocytogenes$; TLR4—3.3 ng/ml $E.\ coli$ K12 LPS; TLR5—30 ng/ml $S.\ typhimurium$ flagellin; TLR8—0.9 μg/ml ssRNA40.

Example 2—RTD-1 Activity is Mediated Through Host Cell Interaction Rather than Antimicrobial Effect Several lines of data demonstrate that the archetypal θ-defensin, RTD-1, exerts its anti-inflammatory effects by interacting with host cells rather than through an antimicrobial effect (29). These findings led to further experiments evaluating the effect of RTDs on the production of TNF-α by human whole blood stimulated with *E. coli* or *S. aureus*. A representative experiment, shown in FIG. 4 (B & C), demonstrates that RTDs 1-5 (FIG. 4A) inhibit *E. coli*-induced TNF-α release; note that even among different θ-defensins there is a notably different inhibitory potency among them. Similar results were obtained in experiments with *S. aureus*. In control experiments, the inventors discovered that unlike many other defensins, the θ-defensins do not interact directly with TNF-α protein, based on results demonstrating that the peptides do not alter the ELISA standard curves and the immunoassay detects only active trimeric TNF-α. Results of these and other experiments suggested that the protective effects of RTD-1 in CLP sepsis (FIG. 3) were due to immunomodulatory activities rather than an antimicrobial effect. Following this result, the inventors stimulated human peripheral blood leukocytes (PBL) with agonists for TLRs 1-9 for 4 h with or without simultaneous addition of 10 μg/ml of RTD-1. As shown in FIG. 5, co-incubation of PBLs with RTD-1 markedly reduced TNF-α release induced by agonists for TLR 2, 4, 5, and 8. Furthermore, RTD-1 also inhibited release of IL-1β and IL-6 stimulated by each agonist, and IL-8 was strongly inhibited in all inductions except in the presence of the TLR2 agonist. RTD-1 had essentially no effect on unstimulated cells (FIG. 5, upper left panel). The effect of RTD-1 treatment on MCP-1 levels varied. The inventors included this chemokine in the analysis because in murine SARS pneumonitis, RTD-1 markedly reduced pulmonary MCP-1 levels (29). This is in agreement with the effect of RTD-1 on PBLs stimulated with viral ssRNA (FIG. 5,). Finally, the inventors further discovered that RTD-1 suppressed expression (>85% reduction) of IL-17A by human PBMCs stimulated ex vivo with enterotoxin-producing *S. aureus* in a dose dependent manner.

Example 3—Inhibition of TACE by θ-Defensins

Figure 6:
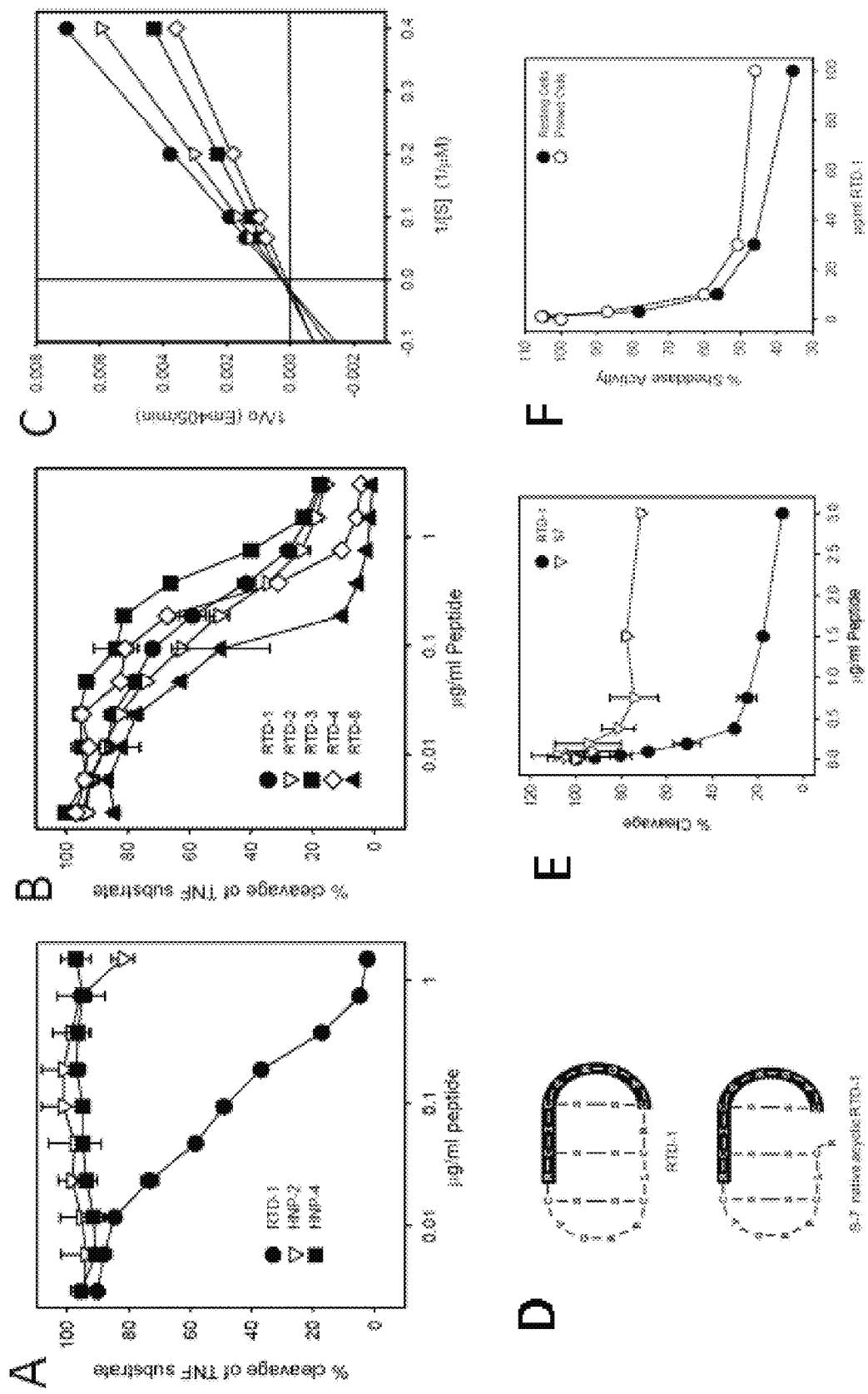
FIG. 6. θ-defensins are competitive inhibitors of TACE. A. Recombinant TACE (rTACE) was incubated with the indicated concentrations of peptides+TACE-specific substrate (Mca-PLAQAV-Dpa-RSSSR-NH$_2$) and enzymatic activity was measured fluorometrically. B. RTDs 1-5 were analyzed for TACE inhibition as in panel A. C. Lineweaver-Burke analysis of RTD-1 inhibition of rTACE at peptide concentrations of 0, 50, 100, and 150 ng/ml. D. Comparison of RTD-1 and "native" acyclic analog (S-7) structures. E. Relative inhibition of rTACE by RTD-1 and RTD-1-S7 analog. F. Inhibition of TACE by RTD-1 on resting or LPS-primed (2 h) THP-1 cells (1).

Since these results demonstrate θ-defensin-mediated inhibition of TNF-α induced by bacteria (FIG. 4), various TLR agonists (FIG. 5), and that measured in animals (see above), one possible mechanism of action was that the activity of TNF-α converting enzyme might be antagonized by θ-defensins. This TNF-α converting enzyme ("TACE", also known as ADAM17, a member of the ADAM (a disintegrin and metalloproteinase) family)), is a sheddase responsible for release of membrane bound TNF-α release. Surprisingly, the inventors found that RTD-1 is a potent inhibitor of recombinant TACE (rTACE) with an IC50 of ~0.1 μg/ml (48 nM). Of note, neither human α-defensin (HNP-2, HNP-4) inhibited rTACE (FIG. 6A), making the activity of θ-defensin unique among defensins. The relative inhibitory activities of natural θ-defensins (RTD 1-5; structures in FIG. 4A) were tested and found to vary over an ~10-fold range of $IC_{50}$ values (FIG. 6B). Of note, the hierarchy of TACE inhibition by RTD 1-5 correlated well with TNF-α inhibition by the peptides in human blood (FIG. 4C). TACE inhibition by RTD-1 was not enhanced by 15 min pre-incubation with TACE, a finding suggestive of rapid binding and competitive inhibition. This was confirmed by double-reciprocal plot analysis of enzyme kinetic data (FIG. 6C), indicating that RTD-1 acts as a pseudosubstrate for TACE. An open chain analog of RTD-1 (S-7; FIG. 6D) was tested for TACE inhibition and was found to have less than 20% of the activity of RTD-1 indicating that the cyclic conformation is required for effective TACE inhibition (FIG. 6E).

Inhibition of TACE was further confirmed in a cell-based assay. RTD-1 was shown to inhibit TACE expressed on resting and LPS-stimulated THP-1 cells (FIG. 6F) using a modification of the assay described by Alvarez-Iglesias et al. (1). The IC50 obtained for RTD-1 in the cell-based assays was ~15 μg/ml (7.4 μM). This compares favorably with the IC50 of the small molecule TACE inhibitor GM6001 (5.5+/−3 μM) in a study of TACE blockade on THP-1 cells (1).

Example 4—θ-Defensins Inhibit ADAM10

Figure 7:
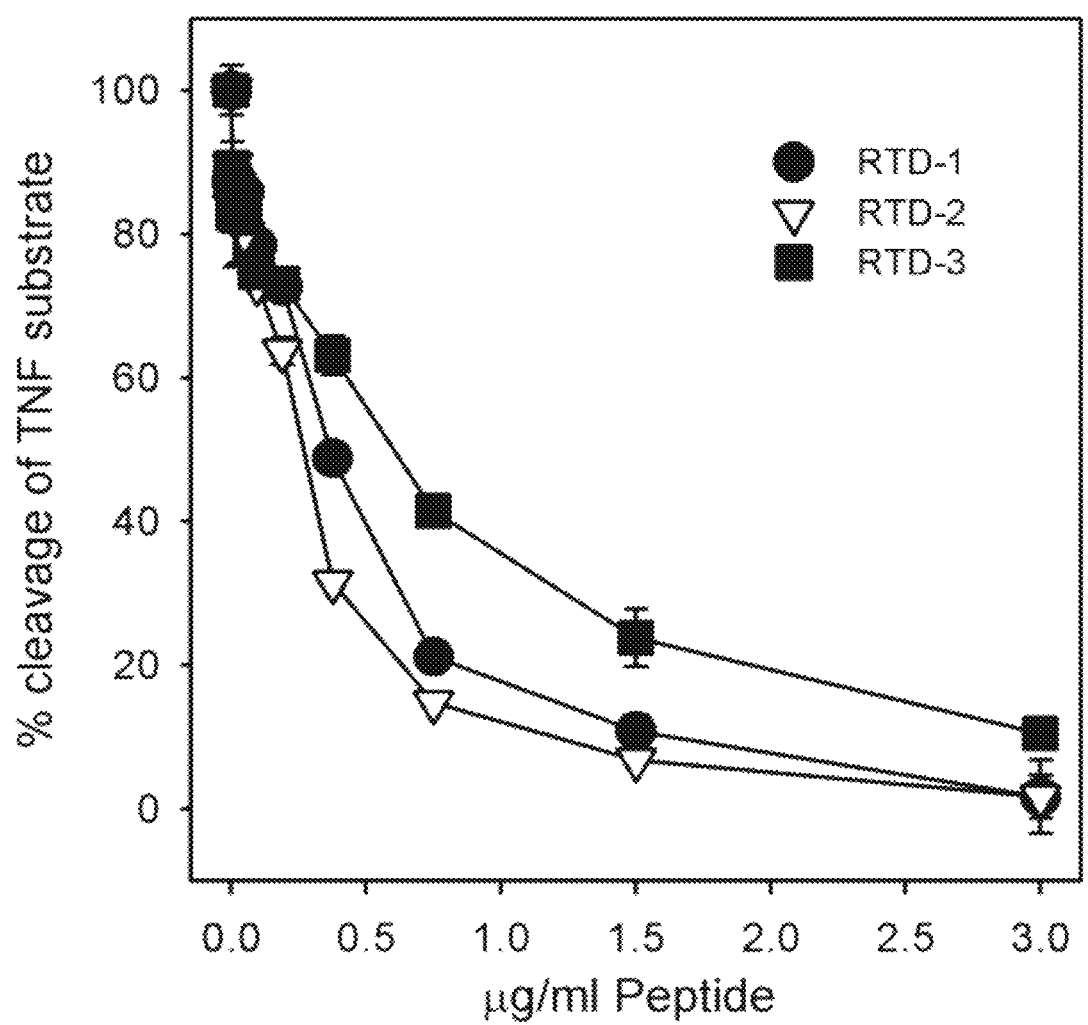
FIG. 7. θ-defensins are potent inhibitors of ADAM10. Recombinant ADAM10 and substrate (Mca-PLAQAV-Dpa-RSSSR-NH$_2$; 0.05 μg/ml) were incubated with RTD 1-3 for 60 min at 37° C. and enzymatic activity was measured fluorometrically.

Various ADAMs have been implicated as regulatory sheddases that release membrane-anchored growth factors, cytokines, and receptors (3). Because ADAMs are implicated in many key biological processes, including the regulation of inflammation and cancer, the identification of ADAM inhibitors is an intense area of research. The inventors established that natural θ-defensins RTD 1-3 inhibit ADAM10 (FIG. 7) with approximately the same IC50 as observed with the inhibition of TACE (see FIG. 6). Thus, θ-defensins are metalloprotease inhibitors of at least two ADAMs.

Example 5—Anti-TNF-α and TACE Inhibition by Mini-θ-Defensins

Figure 8:
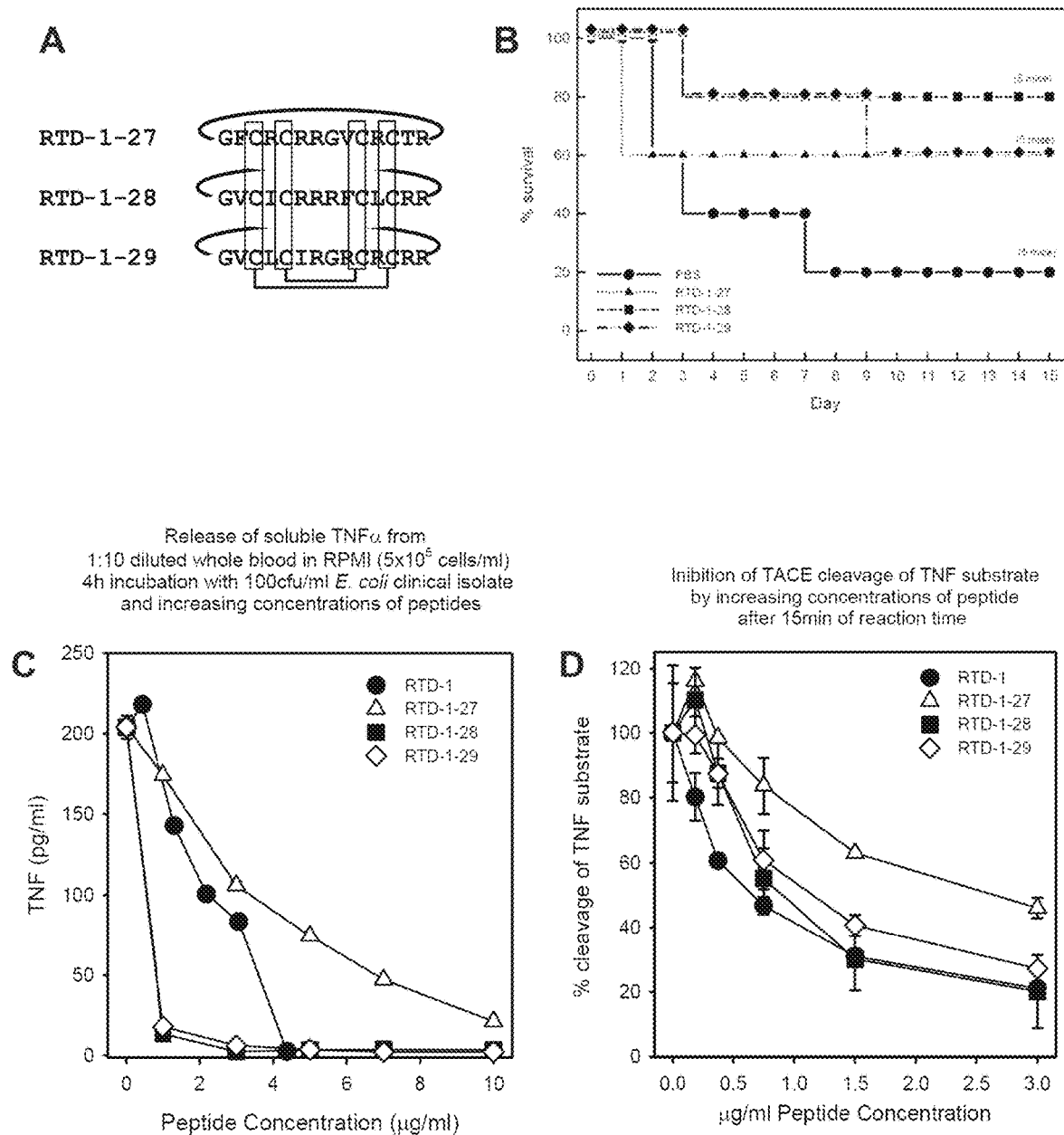
FIG. 8. In vivo efficacy and anti-TNFα and TACE blocking activities of mini-θ-defensins. A. Covalent structures of mini-θ-defensins. B. Efficacy of mini-θ-defensins in CLP sepsis. CLP surgery was performed on BALB/c mice at T=0. Four h post surgery, mice were treated with i.v. PBS (sham control) or 5 mg/kg of the indicated mini-θ-defensin in PBS. Efficacy of treatment was monitored as survival up to 15 days. C. Mini-θ-defensins were evaluated for effects on TNFα release from human whole blood. EDTA-anticoagulated whole blood was diluted 1:10 in RPMI 1640 and incubated with live $E.\ coli$ cells for 4 h with 0-10 μg/ml of RTD-1 (natural θ-defensin) or the three mini-θ-defensins indicated. D. The effect of RTD-1 and three mini-θ-defensins on TACE activity was determined as described in FIG. 5.

Structure-activity analyses of natural and modified θ-defensins suggested certain sequence features that predicted to mediate the anti-inflammatory effects of these peptides. As an example, three tetradecapeptides (mini-θ-defensins) were designed to contain features deemed important for the anti-inflammatory properties of natural θ-defensins. These were incorporated into the sequences of the peptides shown in FIG. 8A. Each peptide was evaluated for its efficacy in murine CLP sepsis. As shown in FIG. 8B, all three mini-θ-defensins reduced lethality in mice compared to the PBS sham treatment. The inventors further evaluated each mini-θ-defensin for its effect on TNF-α release from stimulated human blood (FIG. 8C) and for its inhibitory activity against TACE (FIG. 8D). As the data in FIG. 8 show, the mini-θ-defensins had similar or superior activity to RTD-1 in the CLP assay (compare to FIG. 3), the TNF-α inhibition assay (FIG. 8C), or the TACE inhibition assay (FIG. 8D.)

Mature θ-defensin peptide RTD-1 is a two-stranded beta-sheet that, like the α- and β-defensins, is stabilized by three disulfides. However, the parallel orientation of the RTD-1 disulfide arrangement allows for substantial flexibility around its short axis. Unlike a α- and β-defensins, RTD-1 lacks an amphiphilic topology, and without being bound by any theory, this and other similar structural differences may account for the immune modulatory capabilities unique to θ-defensins.

Example 6—Efficacy of θ-Defensin in Rat Pristane-Induced Arthritis (PIA)

Figure 9:
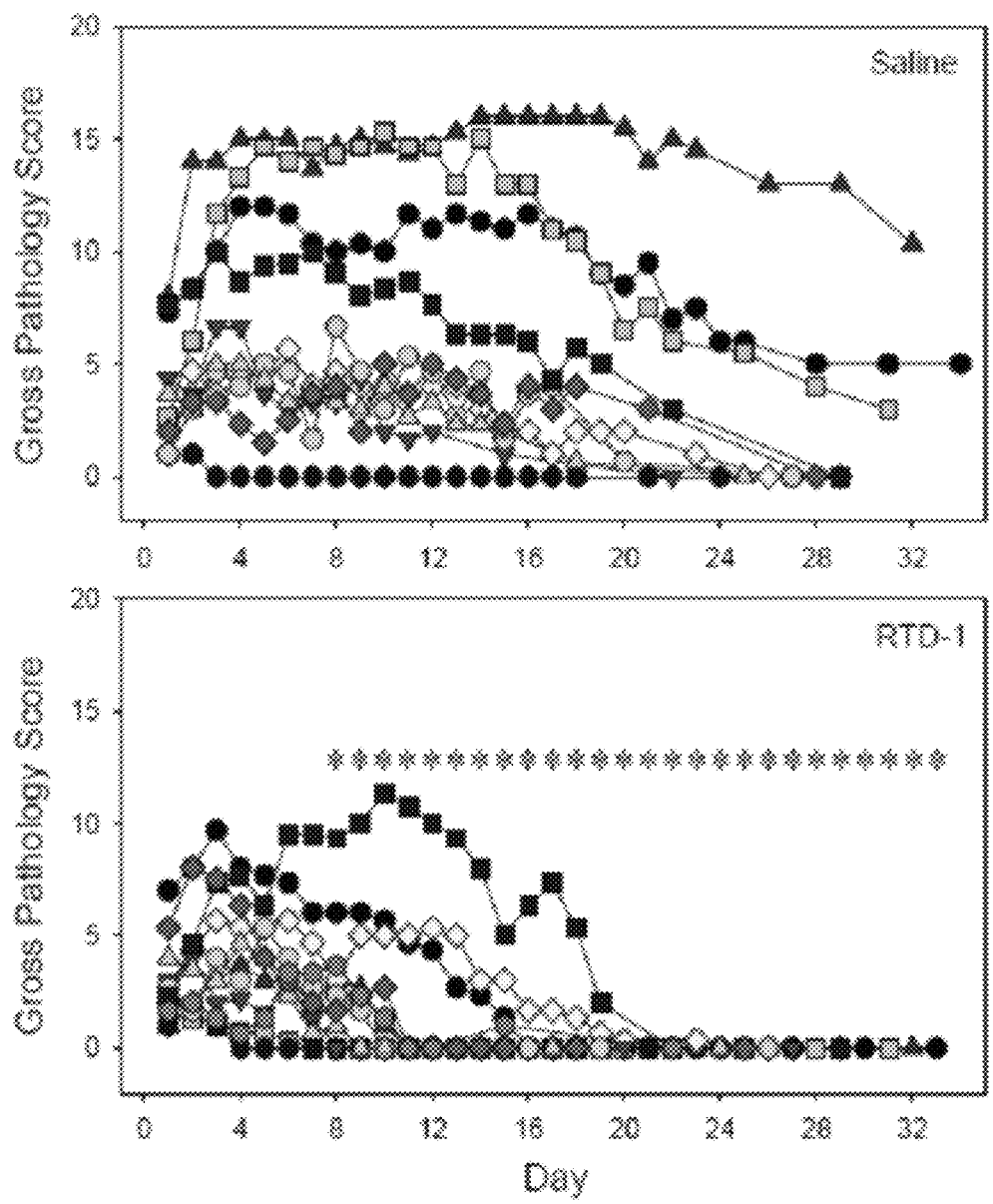
FIG. 9. Effect of RTD-1 in rat Pristane-induced arthritis (PIA). PIA was induced in DA rats as described in the text and were randomized to receive daily i.v. injections of saline (N=10) or 5 mg/kg RTD-1 (N=11). Gross pathology was assessed and scored (20). Each symbol represents gross pathology score of an individual animal. In all cases, RTD-1 treatment induced resolution of joint disease which was accompanied by recovery of normal ambulation.

If blockade of TNF-by θ-defensin in vivo or ex vivo is central to the peptide's anti-inflammatory effects, the inventors believed that it should modulate the course of a disease known to be driven by TNF-α. The inventors proceeded to test the effect of RTD-1 on rats with established PIA. In a representative experiment (N=3), adult Dark Agouti (DA; OlaHsd strain) rats (N=21) were injected subcutaneously with 0.3 ml pristane on day 0 as described by Vingsbo et al. (26). At the first sign of clinical disease (14-21 days; based on the gross pathology scale of Brand et al., ref. (4), animals were alternately assigned to saline (N=10) or RTD-1 treatment (N=11) groups. Blinded administration of saline (0.2-0.25 ml) or RTD-1 (5 mg/kg in 0.2-0.25 ml saline) was performed by daily tail vein injection for up to 14 days unless arthritis severity (scored blindly each day for up to 36 days by three observers) returned to zero earlier (N=1 in saline group; N=8 in RTD-1 group). RTD-1-treated animals had statistically significant (*=p≤0.05 by unpaired two-tailed Student T test) reduction of joint pathology beginning at day 7; FIG. 9. Efficacy was also demonstrated in this model by subcutaneous injection of the same RTD=1 dose and formulation. After cessation of treatment there was no evidence of disease recurrence for at least 45 days.

Example 7—θ-Defensin are Highly Stable

The θ-defensin RTD-1 was incubated at a 50 µg/ml in human plasma, human serum, or 50 mg/ml human serum albumin for 72 hours at room temperature. Quantitative HPLC analysis was performed which showed that more than 95% of the peptide was unaltered under each of the conditions tested. Moreover, θ-defensins are stable to prolonged storage under low (~pH 2.5) or neutral (pH 7.4) conditions.

In summary, θ-defensins possess anti-inflammatory properties that are mediated by the blockade of proinflammatory proteases such as TACE and other metalloenzymes. They are effective in animal models of infectious and non-infectious inflammatory disease, are well tolerated when administered systemically, and are non-immunogenic. In addition, unlike other anti-inflammatory agents, θ-defensins are non-immunosuppressive.

Drug Compositions, Dosages, Dosage Forms and Routes of Administration

The compositions according to the inventive subject matter may be administered using various routes, including orally, parenterally, by inhalation, topically, rectally, nasally, or via an implanted reservoir, wherein the term "parenteral" as used herein includes subcutaneous, intravenous, intramuscular, intraarticular, intrasynovial, intrathecal, intrahepatic, intralesional, and intracranial administration (typically injection or infusion). Preferably, the compositions are administered orally, subcutaneously, intraperitoneally, or intravenously.

For example, sterile injectable forms of contemplated compounds may be aqueous solutions or oleaginous suspensions. These suspensions may be formulated according to techniques known in the art using suitable dispersing or wetting agents and suspending agents. The sterile injectable preparation may also be prepared as a sterile injectable solution or suspension in a non-toxic parenterally acceptable diluent or solvent, for example as a solution in 1,3-butanediol. Among other acceptable vehicles and solvents, especially contemplated liquids include water, Ringer's solution, and isotonic sodium chloride solution. In addition, sterile, fixed oils may be employed as a co-solvent or suspending medium (e.g., natural or synthetic mono- or diglycerides). Fatty acids may also be used, and suitable fatty acids include oleic acid and its glyceride derivatives, olive oil, castor oil, especially in their polyoxyethylated versions. Such oil solutions or suspensions may further contain a long-chain alcohol diluent or dispersant.

In another example, contemplated compounds may be orally administered in any orally acceptable dosage form, including capsules, tablets, aqueous suspensions, or solutions. In the case of tablets for oral use, all pharmaceutically acceptable carriers (e.g., lactose, corn starch, etc) are deemed suitable. Similarly, various lubricating agents may be added (e.g., magnesium stearate). For oral administration in a capsule form, useful diluents include lactose and dried corn starch. When aqueous suspensions are required for oral use, the active ingredient is combined with emulsifying and suspending agents. If desired, certain sweetening, flavoring or coloring agents may also be added.

It is contemplated that the pharmaceutical compositions of the inventive subject matter could be administered topically, especially when the target of treatment includes areas or organs readily accessible by topical application, including diseases of the eye, the skin, the lower intestinal tract, or areas exposed during surgical intervention. There are numerous topical formulations known in the art, and all of such formulations are deemed suitable for use herein.

For topical applications, contemplated compositions may be formulated in a suitable ointment containing the active component suspended or dissolved in one or more carriers. Carriers for topical administration of the compounds of the inventive subject matter include mineral oil, liquid petrolatum, white petrolatum, propylene glycol, polyoxyethylene, polyoxypropylene compound, emulsifying wax and water. Alternatively, the pharmaceutical compositions can be formulated in a suitable lotion or cream containing the active components suspended or dissolved in one or more pharmaceutically acceptable carriers. Suitable carriers include mineral oil, sorbitan monostearate, polysorbate 60, cetyl esters wax, cetearyl alcohol, 2-octyldodecanol, benzyl alcohol and water.

Pharmaceutical compositions according to the inventive subject matter may also be administered by nasal aerosol or inhalation. Such compositions are prepared according to techniques well-known in the art of pharmaceutical formulation and may be prepared as solutions in saline, employing benzyl alcohol or other suitable preservatives, absorption promoters to enhance bioavailability, fluorocarbons, and/or other conventional solubilizing or dispersing agents.

With respect to the amount of contemplated compounds in the composition, it should be recognized that the particular quantity will typically depend on the specific formulation, active ingredient, and desired purpose. Therefore, it should be recognized that the amount of contemplated compounds will vary significantly. However, it is generally preferred that the compounds are present in a minimum amount effective to deliver a therapeutic effect and/or to be visualized in vitro and/or in vivo.

Thus, in most preferred liquid formulations, contemplated compounds will be present in an amount of between about 20 mg/ml to about 30 mg/ml, more typically in an amount of between about 24 mg/ml to about 26 mg/ml, and most about 25 mg/ml. Where the formulation is a solid or a gel, contemplated compounds will be present in an amount of between about 1 mg/g to about 100 mg/g. With respect to a dosage unit, it is generally contemplated that contemplated compounds are administered at a dosage effective to achieve a desired therapeutic effect or at a dosage effective to provide visualization in vitro and/or in vivo.

For both human and non-human mammals, suitable dosing of contemplated compounds should be the range of about 1-10 mg/kg.

In the treatment and/or prophylaxis of inflammatory diseases, it is generally preferred that the compounds or compositions according to the inventive subject matter are formulated in a pharmaceutically acceptable manner. Suitable formulations will preferably include liquid preparations for injection into the anterior and/or posterior chamber of the eye, or for injection into the semicircular canals, cochlea, and/or bony labyrinth of the temporal bone. Alternatively, or additionally, implantable carriers (e.g., biodegradable/dissolving) may be formulated such that the carrier comprises therapeutically effective amounts of the compound or composition, and that the carrier can release the compound or composition in a controlled and predetermined manner. Among other suitable carriers, the release may be time-dependent and/or initiated by irradiation with light of one or more wavelengths.

It is contemplated that pharmaceutical compositions according to the inventive subject matter comprise at least one of contemplated compounds (e.g., one or more of RTD-1-27, RTD-1-28 and RTD-1-29) together with a pharmaceutically acceptable carrier. Depending on the particular use, it should be recognized that formulation, route, and/or administration schedule may vary considerably, and it is generally contemplated that the specific formulation, route, and/or administration is not limiting to the inventive subject matter.

It should be appreciated, however, that the administered dose of the pharmaceutical composition will vary considerably, and a particular dose will at least in part depend on (a) the amount of active ingredient which is effective to achieve a desired therapeutic response, (b) the formulation of contemplated compounds, (c) the route of administration, (d) the pharmacokinetic and pharmacodynamic property of the particular compound, and (e) other factors, including age, sex, weight, general health, and prior medical history of the patient being treated. A person of ordinary skill in the art can readily determine and prescribe the effective amount of the pharmaceutical composition required. For example, a physician could start dosing a patient at levels lower than normally required for a desired therapeutic effect and then increase the dosage until the desired effect is achieved.

It is generally contemplated that the compounds according to the inventive subject matter may be prepared in a formulation for parenteral use, and especially contemplated parenteral formulations will be liquid formulations for injection. Therefore, appropriate formulations will generally include a pharmaceutically acceptable solvent (e.g., sterile isotonic aqueous or non-aqueous solution), and may be prepared as a dispersion, suspension, or emulsion. Alternatively, parenteral formulations may also be provided as a kit that includes contemplated compounds and other components that may be reconstituted to a liquid product prior to use. In still further contemplated aspects, the compounds according to the inventive subject matter may also be administered as recombinant nucleic acid in a manner that allows expression of the compound in a host cell. For example, recombinant nucleic acids may be provided to the target tissue via adenoviral vectors, transfection using lipids or liposomes, electroporation, or other manners well known in the art.

Examples of suitable aqueous and non-aqueous carriers which may be employed in the pharmaceutical compositions include water, ethanol, polyols (e.g., glycerol, propylene glycol, polyethylene glycol, etc.), and suitable mixtures thereof, vegetable oils, and injectable organic esters, such as ethyl oleate. Proper fluidity can be maintained, for example, by the use of coating materials, such as lecithin, by the maintenance of the required particle size in the case of dispersions, and by the use of surfactants. Most typically, suitable fluids are sterile and buffered to maintain a pH appropriate for stability of the active ingredient and site of injection or other use.

Contemplated compounds may be prepared as pharmaceutically acceptable salt(s), which especially include salts of acidic or basic groups which may be present in the contemplated compounds. For example, contemplated compounds that are basic in nature may form a wide variety of salts with various inorganic and organic acids. Suitable acids will provide pharmacologically acceptable anions, including chloride, bromide, iodide, nitrate, sulfate, bisulfate, phosphate, acid phosphate, isonicotinate, acetate, lactate, salicylate, citrate, acid citrate, tartrate, pantothenate, bitartrate, ascorbate, succinate, maleate, gentisinate, fumarate, gluconate, glucaronate, saccharate, formate, benzoate, glutamate, methanesulfonate, ethanesulfonate, benzenesulfonate, p-toluenesulfonate, and pamoate [1,1'-methylene-bis-(2-hydroxy-3-naphthoate)] anions. Similarly, compounds that are acidic in nature may form base salts with various pharmacologically acceptable cations, and especially suitable cations include alkali metal or alkaline earth metal ions (e.g., sodium and potassium cations).

It is still further especially contemplated that compounds according to the inventive subject matter may also be prepared as prodrugs, and all known manners and types of prodrugs are considered suitable for use herein, so long as such prodrug will increase the concentration of the drug (or metabolite of the prodrug) at a target organ or target cell.

For example, where the compounds have a free amino, amido, hydroxy, thio, or carboxylic group, it is contemplated that such groups can be employed to covalently and releasably bind a moiety that converts the drug into a prodrug. Therefore, prodrugs particularly include those in which contemplated compounds forms an ester, amide, or disulfide bond with another cleavable moiety. Such moieties may assist in organ or cell-specific delivery of the drug. For instance, a carboxyl group can be derivatized to form an amide or alkyl ester, which may include an ether, amine-, and/or carboxylic acid group. Free hydroxy groups may be derivatized using hemisuccinates, phosphate esters, dimethylaminoacetates, and phosphoryloxymethyloxycarbonyls, as outlined in D. Fleisher, R. Bong, B. H. Stewart, Advanced Drug Delivery 40 Reviews (1996) 19, 115. Carbamate prodrugs of hydroxy and amino groups are also included, as are carbonate prodrugs and sulfate esters of hydroxy groups. Derivatization of hydroxy groups as (acyloxy)methyl and (acyloxy)ethylethers, wherein the acyl group may be an alkyl ester (optionally substituted), or where the acyl group is an amino acid ester are also contemplated (Prodrugs of this type are described in R. P. Robinson et al., J. Medicinal Chemistry (1996) 39: p. 10).

Still further, it should also be recognized that contemplated compounds may be metabolized in a cell or extracellular compartment, and that such metabolites may exhibit the same or different pharmacological effect. For example, contemplated compounds may be phosphorylated and thus be more active than the parent compound. On the other hand, reduction or glycosylation may affect bioavailability of contemplated compounds. Consequently, contemplated compounds will not only include those as described above, but also include metabolites thereof.

Miscellaneous

The various methods and techniques described above provide a number of ways to carry out methods relating to the inventive subject matter. Of course, it is to be understood that not necessarily all objectives or advantages described may be achieved in accordance with any particular embodiment described herein. Thus, for example, those skilled in the art will recognize that the methods can be performed in a manner that achieves or optimizes one advantage or group of advantages as taught herein without necessarily achieving other objectives or advantages as may be taught or suggested herein. A variety of advantageous and disadvantageous alternatives are mentioned herein. It is to be understood that some preferred embodiments specifically include one, another, or several advantageous features, while others specifically exclude one, another, or several disadvantageous features, while still others specifically mitigate a present disadvantageous feature by inclusion of one, another, or several advantageous features.

Furthermore, the skilled artisan will recognize the applicability of various features from different embodiments. Similarly, the various elements, features and steps discussed above, as well as other known equivalents for each such element, feature or step, can be mixed and matched by one of ordinary skill in this art to perform methods in accordance with principles described herein. Among the various elements, features, and steps some will be specifically included and others specifically excluded in diverse embodiments.

Although the inventive subject matter has been disclosed in the context of certain embodiments and examples, it will be understood by those skilled in the art that the embodiments of the inventive subject matter extend beyond the specifically disclosed embodiments to other alternative embodiments and/or uses and modifications and equivalents thereof.

Many variations and alternative elements have been disclosed in embodiments of the inventive subject matter. Still further variations and alternate elements will be apparent to one of skill in the art. Among these variations, without limitation, are the sources of cyclic peptides, including θ-defensin, methods of preparing, isolating, or purifying θ-defensins, analogs and derivatives thereof, methods of treating various disease and/or conditions using θ-defensins, analogs and derivatives thereof, techniques and composition and use of solutions used therein, and the particular use of the products created through the teachings herein. Various embodiments can specifically include or exclude any of these variations or elements.

In some embodiments, the numbers expressing quantities of ingredients, properties such as concentration, reaction conditions, and so forth, used to describe and claim certain embodiments are to be understood as being modified in some instances by the term "about." Accordingly, in some embodiments, the numerical parameters set forth in the written description and attached claims are approximations that can vary depending upon the desired properties sought to be obtained by a particular embodiment. In some embodiments, the numerical parameters should be construed in light of the number of reported significant digits and by applying ordinary rounding techniques. Notwithstanding that the numerical ranges and parameters setting forth the broad scope of some embodiments are approximations, the numerical values set forth in the specific examples are reported as precisely as practicable. The numerical values presented in some embodiments may contain certain errors necessarily resulting from the standard deviation found in their respective testing measurements.

As used in the description herein and throughout the claims that follow, the meaning of "a," "an," and "the" includes plural reference unless the context clearly dictates otherwise. Also, as used in the description herein, the meaning of "in" includes "in" and "on" unless the context clearly dictates otherwise.

The recitation of ranges of values herein is merely intended to serve as a shorthand method of referring individually to each separate value falling within the range. Unless otherwise indicated herein, each individual value is incorporated into the specification as if it were individually recited herein. All methods described herein can be performed in any suitable order unless otherwise indicated herein or otherwise clearly contradicted by context. The use of any and all examples, or exemplary language (e.g. "such as") provided with respect to certain embodiments herein is intended merely to better illuminate the inventive subject matter, and does not pose a limitation on the scope of the claimed inventions. No language in the specification should be construed as indicating any non-claimed element essential to the practice of the claimed inventions.

Groupings of alternative elements or embodiments of the inventive subject matter disclosed herein are not to be construed as limitations. Each group member can be referred to and claimed individually or in any combination with other members of the group or other elements found herein. One or more members of a group can be included in, or deleted from, a group for reasons of convenience and/or patentability. When any such inclusion or deletion occurs, the specification is herein deemed to contain the group as modified thus fulfilling the written description of all Markush groups used in the appended claims.

Preferred embodiments of this inventive subject matter are described herein, including the best mode known to the inventors for carrying out the claimed inventions. Variations on those preferred embodiments will become apparent to those of ordinary skill in the art upon reading the foregoing description. It is contemplated that skilled artisans can employ such variations as appropriate, and the claimed inventions can be practiced otherwise than specifically described herein. Accordingly, the claimed inventions are to be interpreted as including all modifications and equivalents of the recited subject matter as permitted by applicable law. Moreover, any combination of the above-described elements in all possible variations thereof is encompassed by the corresponding claimed inventions unless otherwise indicated herein or otherwise clearly contradicted by context.

Furthermore, numerous references have been made to patents and printed publications throughout this specification. Each of the above cited references and printed publications are herein individually incorporated by reference in their entirety.

It is to be understood that the embodiments disclosed herein are illustrative of the principles of the inventive subject matter. Thus, by way of example, but not of limitation, alternative configurations of the inventive subject matter can be utilized in accordance with the teachings herein. Accordingly, embodiments of the inventive subject matter are not limited to that precisely as shown and described.

REFERENCES

1. Alvarez-Iglesias, M., G. Wayne, K. P. O'Dea, A. Amour, and M. Takata. 2005. Continuous real-time measurement of tumor necrosis factor-alpha converting enzyme activity on live cells. Lab Invest 85:1440-1448.
2. Berkestedt, I., H. Herwald, L. Ljunggren, A. Nelson, and M. Bodelsson. 2010. Elevated plasma levels of antimicrobial polypeptides in patients with severe sepsis. J Innate Immun 2:478-482.
3. Blobel, C. P. 2005. ADAMs: key components in EGFR signalling and development. Nat Rev Mol Cell Biol 6:32-43.
4. Brand, D. D., A. H. Kang, and E. F. Rosloniec. 2004. The mouse model of collagen-induced arthritis. Methods Mol Med 102:295-312.
5. Cole, A. M., T. Hong, L. M. Boo, T. Nguyen, C. Zhao, G. Bristol, J. A. Zack, A. J. Waring, O. O. Yang, and R. I. Lehrer. 2002. Retrocyclin: a primate peptide that protects cells from infection by T- and M-tropic strains of HIV-1. Proc Natl Acad Sci USA 99:1813-1818.
6. Cole, A. M., and R. I. Lehrer. 2003. Minidefensins: antimicrobial peptides with activity against HIV-1. Curr Pharm Des 9:1463-1473.
7. Feldmann, M., and R. N. Maini. 2003. Lasker Clinical Medical Research Award. TNF defined as a therapeutic target for rheumatoid arthritis and other autoimmune diseases. Nat Med 9:1245-1250.
8. Firestein, G. S. 2003. Evolving concepts of rheumatoid arthritis. Nature 423:356-361.
9. Garcia, A. E., G. Osapay, P. A. Tran, J. Yuan, and M. E. Selsted. 2008. Isolation, synthesis, and antimicrobial activities of naturally occurring theta-defensin isoforms from baboon leukocytes. Infect Immun 76:5883-5891.
10. Giacometti, A., O. Cirioni, R. Ghiselli, F. Mocchegiani, G. D'Amato, R. Circo, F. Orlando, B. Skerlavaj, C. Silvestri, V. Saba, M. Zanetti, and G. Scalise. 2004. Cathelicidin peptide sheep myeloid antimicrobial peptide-29 prevents endotoxin-induced mortality in rat models of septic shock. Am J Respir Crit Care Med 169:187-194.
11. Giacometti, A., O. Cirioni, R. Ghiselli, F. Mocchegiani, M. S. Del Prete, C. Viticchi, W. Kamysz, L. E. E, V. Saba, and G. Scalise. 2002. Potential therapeutic role of cationic peptides in three experimental models of septic shock. Antimicrob Agents Chemother 46:2132-2136.
12. Hubbard, W. J., M. Choudhry, M. G. Schwacha, J. D. Kerby, L. W. Rue, 3rd, K. I. Bland, and I. H. Chaudry. 2005. Cecal ligation and puncture. Shock 24 Suppl 1:52-57.
13. McInnes, I. B., and J. R. O'Dell. 2010. State-of-the-art: rheumatoid arthritis. Ann Rheum Dis 69:1898-1906.
14. Moss, M. L., L. Sklair-Tavron, and R. Nudelman. 2008. Drug insight: tumor necrosis factor-converting enzyme as a pharmaceutical target for rheumatoid arthritis. Nat Clin Pract Rheumatol 4:300-309.
15. Motzkus, D., S. Schulz-Maronde, A. Heitland, A. Schulz, W. G. Forssmann, M. Jubner, and E. Maronde. 2006. The novel beta-defensin DEFB123 prevents lipopolysaccharide-mediated effects in vitro and in vivo. Faseb J 20:1701-1702.
16. Murphy, G., and H. Nagase. 2008. Reappraising metalloproteinases in rheumatoid arthritis and osteoarthritis: destruction or repair? Nat Clin Pract Rheum 4:128-135.
17. Murumkar, P. R., S. DasGupta, S. R. Chandani, R. Giridhar, and M. R. Yaday. 2010. Novel TACE inhibitors in drug discovery: a review of patented compounds. Expert Opin Ther Pat 20:31-57.
18. Panyutich, A. V., E. A. Panyutich, V. A. Krapivin, E. A. Baturevich, and T. Ganz. 1993. Plasma defensin concentrations are elevated in patients with septicemia or bacterial meningitis. J Lab Clin Med 122:202-207.
19. Rosenfeld, Y., and Y. Shai. 2006. Lipopolysaccharide (Endotoxin)-host defense antibacterial peptides interactions: role in bacterial resistance and prevention of sepsis. Biochim Biophys Acta 1758:1513-1522.
20. Rosloniec, E. F., M. Cremer, A. H. Kang, L. K. Myers, and D. D. Brand. 2010. Collagen-induced arthritis. Curr Protoc Immunol Chapter 15:Unit 15 15 11-25.
21. Selsted, M. E. 2004. Theta-defensins: cyclic antimicrobial peptides produced by binary ligation of truncated alpha-defensins. Curr Protein Pept Sci 5:365-371.
22. Tang, Y. Q., J. Yuan, G. Osapay, K. Osapay, D. Tran, C. J. Miller, A. J. Ouellette, and M. E. Selsted. 1999. A cyclic antimicrobial peptide produced in primate leukocytes by the ligation of two truncated alpha-defensins. Science 286:498-502.
23. Tongaonkar, P., P. Tran, K. Roberts, J. Schaal, G. Osapay, D. Tran, A. J. Ouellette, and M. E. Selsted. 2011. Rhesus macaque {theta}-defensin isoforms: expression, antimicrobial activities, and demonstration of a prominent role in neutrophil granule microbicidal activities. J Leukoc Biol 89:283-290.
24. Tran, D., P. Tran, K. Roberts, G. Osapay, J. Schaal, A. Ouellette, and M. E. Selsted. 2008. Microbicidal properties and cytocidal selectivity of rhesus macaque theta defensins. Antimicrob Agents Chemother 52:944-953.
25. Tran, D., P. A. Tran, Y. Q. Tang, J. Yuan, T. Cole, and M. E. Selsted. 2002. Homodimeric theta-defensins from rhesus macaque leukocytes: isolation, synthesis, antimicrobial activities, and bacterial binding properties of the cyclic peptides. J Biol Chem 277:3079-3084.
26. Vingsbo, C., P. Sahlstrand, J. G. Brun, R. Jonsson, T. Saxne, and R. Holmdahl. 1996. Pristane-induced arthritis in rats: a new model for rheumatoid arthritis with a chronic disease course influenced by both major histocompatibility complex and non-major histocompatibility complex genes. Am J Pathol 149:1675-1683.
27. Wang, W., A. M. Cole, T. Hong, A. J. Waring, and R. I. Lehrer. 2003. Retrocyclin, an antiretroviral theta-defensin, is a lectin. J Immunol 170:4708-4716.
28. Wang, W., S. M. Owen, D. L. Rudolph, A. M. Cole, T. Hong, A. J. Waring, R. B. Lal, and R. I. Lehrer. 2004. Activity of alpha- and theta-defensins against primary isolates of HIV-1. J Immunol 173:515-520.
29. Wohlford-Lenane, C. L., D. K. Meyerholz, S. Perlman, H. Zhou, D. Tran, M. E. Selsted, and P. B. McCray, Jr. 2009. Rhesus theta-defensin prevents death in a mouse model of severe acute respiratory syndrome coronavirus pulmonary disease. J Virol 83:11385-11390.
30. Moss M. L., A. Stoeck, W. Yan, P. J. Dempsey. 2008. ADAM10 as a target for anti-cancer therapy. Curr Pharm Biotechnol 9:2-8.
31. Molina M. A., J. Codony-Servat, J. Albanell, F. Rojo, J. Arribas, J. Baselga. 2001. Trastuzumab (herceptin), a humanized anti-Her2 receptor monoclonal antibody, inhibits basal and activated Her2 ectodomain cleavage in breast cancer cells. Cancer Res 61:4744-9.

What is claimed is:

1. A method of inhibiting a metalloprotease and a cysteine protease in a subject in need thereof, comprising:
    injectably administering to the subject in need thereof a θ-defensin in an amount effective to inhibit the metalloprotease and the cysteine protease; wherein the θ-defensin is administered intravenously, subcutaneously, or intraperitoneally; and wherein the administration reduces TNF-alpha mediated inflammation in the subject.

2. The method of claim 1, wherein the θ-defensin is a mini-θ-defensin.

3. The method of claim 1, wherein the θ-defensin is selected from the group consisting of SEQ. ID NO. 8, SEQ. ID NO. 11, SEQ. ID NO. 12, SEQ. ID NO.13, SEQ. ID NO. 14, SEQ. ID NO. 15, SEQ. ID NO. 16, SEQ. ID NO. 17, and SEQ. ID NO. 18.

4. The method of claim 1, wherein the θ-defensin is selected from the group consisting of SEQ. ID NO. 8, SEQ. ID NO. 14, and SEQ. ID NO. 15.

5. The method of claim 1, wherein the mini-θ-defensin is selected from the group consisting of SEQ. ID NO. 11, SEQ. ID NO. 12, and SEQ. ID NO.13.

6. The method of claim 1, wherein the mini-θ-defensin is SEQ. ID NO. 12.

7. The method of claim 1, wherein the cysteine protease is Cathepsin-C.

8. The method of claim 1, wherein the θ-defensin is formulated for injection.

9. A method of inhibiting a metalloprotease or a cysteine protease in a subject in need thereof, comprising:
    administering to the subject in need thereof a θ-defensin in an amount effective to inhibit the metalloprotease or the cysteine protease, wherein the θ-defensin is a mini-θ-defensin.

10. The method of claim 9, wherein the mini-θ-defensin is selected from the group consisting of SEQ. ID NO. 11, SEQ. ID NO. 12, and SEQ. ID NO.13.

11. The method of claim 10, wherein the mini-θ-defensin is SEQ. ID NO. 12.

12. The method of claim 1, wherein the θ-defensin is administered by intravenous injection.

13. The method of claim 1, wherein the θ-defensin is administered by intravenous infusion.

14. The method of claim 1, wherein the θ-defensin is administered by subcutaneous injection.

15. The method of claim 1, wherein the θ-defensin is administered by intraperitoneal injection.

* * * * *